US007279587B2

(12) United States Patent
Odell et al.

(10) Patent No.: US 7,279,587 B2
(45) Date of Patent: *Oct. 9, 2007

(54) PHOTOINITIATOR WITH PHASE CHANGE PROPERTIES AND GELLANT AFFINITY

(75) Inventors: Peter G. Odell, Mississauga (CA); Eniko Toma, Mississauga (CA); Jennifer L. Belelie, Oakville (CA)

(73) Assignee: Xerox Corporation, Stamford, CT (US)

( * ) Notice: Subject to any disclaimer, the term of this patent is extended or adjusted under 35 U.S.C. 154(b) by 13 days.

This patent is subject to a terminal disclaimer.

(21) Appl. No.: 11/290,207

(22) Filed: Nov. 30, 2005

(65) Prior Publication Data

US 2007/0123723 A1    May 31, 2007

(51) Int. Cl.
*C07C 231/00* (2006.01)
(52) U.S. Cl. .......................................... 554/37; 560/169
(58) Field of Classification Search .................. 554/37, 554/7; 560/169
See application file for complete search history.

(56) References Cited

U.S. PATENT DOCUMENTS

| | | | |
|---|---|---|---|
| 3,653,932 A | 4/1972 | Berry et al. | |
| 4,390,369 A | 6/1983 | Merritt et al. | |
| 4,484,948 A | 11/1984 | Merritt et al. | |
| 4,684,956 A | 8/1987 | Ball | |
| 4,851,045 A | 7/1989 | Taniguchi | |
| 4,889,560 A | 12/1989 | Jaeger et al. | |
| 4,889,761 A | 12/1989 | Titterington et al. | |
| 5,006,170 A | 4/1991 | Schwarz et al. | |
| 5,151,120 A | 9/1992 | You et al. | |
| 5,221,335 A | 6/1993 | Williams et al. | |
| 5,372,852 A | 12/1994 | Titterington et al. | |
| 5,496,879 A | 3/1996 | Griebel et al. | |
| 5,621,022 A | 4/1997 | Jaeger et al. | |
| 5,804,671 A | 9/1998 | Dones et al. | |
| 5,889,076 A | 3/1999 | Dones et al. | |
| 6,239,189 B1 | 5/2001 | Narayan et al. | |
| 6,316,517 B1 | 11/2001 | Dones et al. | |
| 6,467,897 B1 | 10/2002 | Wu et al. | |
| 6,586,492 B1 | 7/2003 | Caiger et al. | |
| 6,896,937 B2 | 5/2005 | Woudenberg | |
| 2003/0036587 A1 | 2/2003 | Kozak | |

FOREIGN PATENT DOCUMENTS

| | | |
|---|---|---|
| EP | 0206286 B1 | 5/1990 |
| EP | 0187352 B1 | 6/1991 |
| WO | WO 94/04619 | 3/1994 |
| WO | WO 0/3079002 A2 * | 9/2003 |

OTHER PUBLICATIONS

Copending U.S. Appl. No. 11/018,378, filed Dec. 22, 2004, entitled "Curable Phase Change Ink Composition," by Peter G. Odell et al.

Copending U.S. Appl. No. 11/004,761, filed Dec. 4, 2004, entitled "Curable Trans-1,2-Cycolhexane Bis[urea-urethane] Compounds," by Rina Carlini et al.

Copending U.S. Appl. No. 11/181,632, filed Jul. 13, 2005, entitled "Ink Carriers, Phase Change Inks Including Same and Methods for Making Same," by Adela Goredema et al.

Copending U.S. Appl. No. (not yet assigned), filed concurrently herewith, entitled "Phase Change Inks Containing Curable Isocyanate-Derived Compounds," by Jeffery H. Banning et al.

Copending U.S. Appl. No. (not yet assigned), filed concurrently herewith, entitled "Phase Change Inks Containing Curable Isocyanate-Derived Compounds and Phase Change Inducing Components," by Jennifer L. Belelie et al.

Copending U.S. Appl. No. (not yet assigned), filed concurrently herewith, entitled "Phase Change Inks Containing Compounds Derived from Isocyanate, Unsaturated Alcohol, and Polyol," with the named inventors Jennifer L. Belelie, Rina Carlini.

Copending U.S. Appl. No. (not yet assigned), filed concurrently herewith, entitled "Radiation Curable Phase Change Inks Containing Curable Epoxy-Polyamide Composite Gellants," by Rina Carlini et al.

Copending U.S. Appl. No. (not yet assigned), filed concurrently herewith, entitled "Radiation Curable Phase Change Inks Containing Gellants," by Peter G. Odell et al.

Copending U.S. Appl. No. (not yet assigned), filed concurrently herewith, entitled "Phase Change Inks," Peter Gordon Odell et al.

Copending U.S. Appl. No. (not yet assigned), filed concurrently herewith, entitled "Phase Change Inks and Methods for Making Same," by Adela Goredema et al.

Copending U.S. Appl. No. (not yet assigned), filed concurrently herewith, entitled "Ink Carriers Containing Nanoparticles, Phase Change Inks Including Same and Methods for Making Same," by Marcel P. Breton et al.

Copending U.S. Appl. No. (not yet assigned), filed concurrently herewith, entitled "Black Inks and Method for Making Same," by Marcel P. Breton et al.

(Continued)

*Primary Examiner*—Johann Richter
*Assistant Examiner*—Sudhakar Katakam
(74) *Attorney, Agent, or Firm*—Judith L. Byorick

(57) ABSTRACT

Disclosed is a compound of the formula

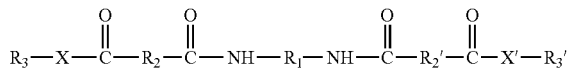

wherein $R_1$ is an alkylene, arylene, arylalkylene, or alkylarylene group, $R_2$ and $R_2'$ each independently of the other, are alkylene, arylene, arylalkylene, or alklarylene groups, $R_3$ and $R_3'$ each, independently of the other, are either (a) photoinitiating groups, or (b) groups which are alkyl, aryl, arylalkyl, or alkylaryl groups, provide that at least one of $R_3$ and $R_3'$ is a photoinitiating group, and X and X' each, independently of the other, is an oxygen atom or a group of the formula —$NR_4$—, wherein $R_4$ is a hydrogen atom, an alkyl group, an aryl group, or an alkylaryl group.

23 Claims, No Drawings

OTHER PUBLICATIONS

Copending U.S. Appl. No. (not yet assigned), filed concurrently herewith, entitled "Ink Carriers, Phase Change Inks Including Same and Methods for Making Same," by Marcel P. Breton et al.

Copending U.S. Appl. No. (not yet assigned), filed concurrently herewith, entitled "Curable Overcoat for Wax-Based Inks," by Jennifer L. Belelie et al.

Copending U.S. Appl. No. (not yet assigned), filed concurrently herewith, entitled "Radiation Curable Ink Containing a Curable Wax," by Jennifer Lynne Belelie et al.

Copending U.S. Appl. No. (not yet assigned), filed concurrently herewith, entitled "Curable Phase Change Compositions and Methods for Using Such Compositions," by Jennifer L. Belelie et al.

Copending U.S. Appl. No. (not yet assigned), filed concurrently herewith, entitled "Overcoat Compositions, Oil-Based Ink Compositions, and Processes for Ink-Jet Recording Using Overcoat Compositions and Oil-Based Ink Compositions," by Gregory J. Kovacs et al.

Copending U.S. Appl. No. (not yet assigned), filed concurrently herewith, entitled "Pre-Treatment Compositions, Oil-Based Ink Compositions, and Processes for Ink-Jet Recording Using Pre-Treatment Compositions and Oil-Based Ink Compositions," by Gregory J. Kovacs et al.

Copending U.S. Appl. No. (not yet assigned), filed concurrently herewith, entitled "Curable Amide Gellant Compounds," Eniko Toma et al.

Copending U.S. Appl. No. (not yet assigned), filed concurrently herewith, entitled "Phase Change Inks Containing Curable Amide Gellant Compounds," by Eniko Toma et al.

Copending U.S. Appl. No. (not yet assigned), filed concurrently herewith, entitled "Process for Making Curable Amide Gellant Compounds," by Eniko Toma et al.

Copending U.S. Appl. No. (not yet assigned), filed concurrently herewith, entitled "Method for Preparing Curable Amide Gellant Compounds," by Jennifer L. Belelie et al.

Copending U.S. Appl. No. (not yet assigned), filed concurrently herewith, entitled "Phase Change Inks Containing Photoinitiator With Phase Change Properties and Gellant Affinity," by Peter G. Odell et al.

English abstract for German Patent Publication DE 4205636AL.

English abstract for German Patent Publication DE 4205713AL.

* cited by examiner

PHOTOINITIATOR WITH PHASE CHANGE PROPERTIES AND GELLANT AFFINITY

CROSS-REFERENCE TO RELATED APPLICATIONS

Copending Application U.S. Ser. No. 11/018,378, filed Dec. 22, 2004, entitled "Curable Phase Change Ink Composition," with the named inventors Peter G. Odell, Marcel P. Breton, Christine E. Bedford, and Chris A. Wagner, the disclosure of which is totally incorporated herein by reference, discloses ink compositions that comprise one or more radiation curable oil soluble components and one or more thermal solvents, as well as methods of preparing such ink compositions and methods of using such ink compositions.

Copending Application U.S. Ser. No. 11/004,761, filed Dec. 4, 2004, entitled "Curable Trans-1,2-Cyclohexane Bis (urea-urethane) Compounds," with the named inventors Rina Carlini, Eniko Toma, Peter G. Odell, and Jeffery H. Banning, the disclosure of which is totally incorporated herein by reference, discloses curable trans-1,2-cyclohexane bis(ureaurethane) compounds of the formulae

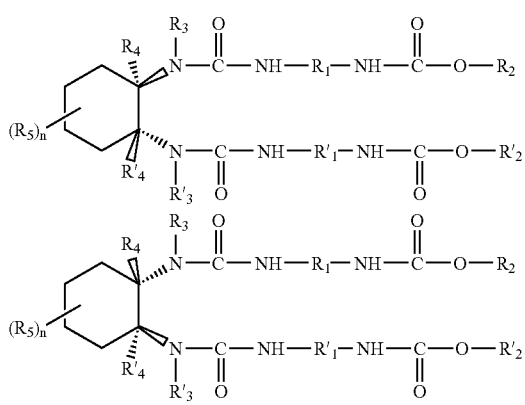

wherein $R_1$ and $R'_1$ each, independently of the other, are alkylene, arylene, arylalkylene, or alkylarylene groups, $R_2$ and $R'_2$ each, independently of the other, are alkyl, aryl, arylalkyl, or alkylaryl groups, $R_3$ and $R'_3$ each, independently of the other, are hydrogen atoms or alkyl groups, $R_4$ and $R'_4$ each, independently of the other, are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending Application U.S. Ser. No. 11/181,632, filed Jul. 13, 2005, entitled "Ink Carriers, Phase Change Inks Including Same and Methods for Making Same," with the named inventors Adela Goredema, Christine E. Bedford, Marcel P. Breton, and Chris A. Wagner, the disclosure of which is totally incorporated herein by reference, discloses an ink carrier comprising an ester terminated oligo-amide material having a substantially low polydispersity. This ink carrier can be combined with a colorant to produce an ink composition.

Copending Application U.S. Ser. No. 11/289,931, filed concurrently herewith, entitled "Phase Change Inks Containing Curable Isocyanate-Derived Compounds," with the named inventors Jeffery H. Banning, Jennifer L. Belelie, Peter G. Odell, Rina Carlini, Jule W. Thomas, Donald R. Titterington, Paul F. Smith, Stephan V. Drappel, and Chris A. Wagner, the disclosure of which is totally incorporated herein by reference, discloses a phase change ink comprising a colorant an initiator, and a phase change ink carrier, said carrier comprising (A) a urethane which is the reaction product at a mixture comprising (1) an isocyanate; and (2) an alcohol selected from the group consisting of 1,4 butanediol vinyl ether, 2-allyloxy ethanol, 1,4-cyclohexanedimethanol vinyl ether, ethylene glycol vinyl ether, di(ethylene glycol) vinyl ether, and mixtures thereof; (B) a compound which is the reaction product of a mixture comprising (1) an isocyanate; and (2) a component comprising (a) an amine having at least one ethylenic unsaturation; (b) an acid having at least one ethylenic unsaturation; (c) a mixture of an amine having at least one ethylenic unsaturation and an alcohol having at least one ethylenic unsaturation; (d) a mixture of an acid having at least one ethylenic unsaturation and an alcohol having at least one ethylenic unsaturation; or (e) mixtures thereof; or (C) a mixitre of (A) and (B); said ink being curable upon exposure to ultraviolet radiation.

Copending Application U.S. Ser. No. 11/289,883, filed concurrently herewith, entitled "Phase Change Inks Containing Compounds Derived from Isocyanate, Unsaturated Alcohol, and Polyol," with the named inventors Jennifer L. Belelie, Rina Carlini, and Eniko Toma, the disclosure of which is totally incorporated herein by reference, discloses a phase change ink comprising a colorant an initiator, and a phase change ink carrier, said carrier comprising (A) a first isocyanate-derived compound which is the reaction product of a mixture comprising (1) an isocyanate; and (2) a component comprising (a) an alcohol having at least one ethylenic unsaturation; (b) an amine having at least one ethylenic unsaturation; (c) an acid having at least one ethylenic unsaturation; or (d) mixtures thereof, (B) a second isocyanate-derived compound which is the reaction product of (1) a diisocyanate; (2) a monoalcohol having exactly one hydroxyl group and having at least one ethylenic unsaturation; and (3) a polyol having two or more hydroxyl groups, (C) an optional phase change inducing component said phase change inducing component containing at least one hydroxyl group, said phase change inducing component having a melting point of about 40° C. or higher, and (D) an optional curable viscosity modifying ester, said ink being curable upon exposure to ultraviolet radiation.

Copending Application U.S. Ser. No. 11/289,473, filed concurrently herewith, entitled "Radiation Curable Phase Change Inks Containing Curable Epoxy-Polyamide Composite Gellants," with the named inventors Rina Carlini, Eniko Toma, Peter G. Odell, and Vaisnavi Siritharan, the disclosure of which is totally incorporated herein by reference, discloses a radiation curable phase change ink preferably used in piezoelectric ink jet devices including an ink vehicle that includes at least one curable epoxy-polyamide gellant and at least one colorant. The use of the gellant enables the ink to form a gel state having a viscosity of at least $10^3$ mPa·s at very low temperatures of about 25° C. to about 100° C. The ink may thus be jetted, for example onto an intermediate transfer member surface or directly to an image receiving substrate, at very low jetting temperatures ot for example, about 40° C. to about 110° C. In a preferred method of forming an image with the ink, the ink is heated to a first temperature at which the ink may be jetted, jetted onto an image receiving or intermediate transfer member surface maintained at a second temperature at which the ink forms in a gel state, if appropriate subsequently transferred from the intermediate transfer member surface to an image receiving substrate, and exposed to radiation energy to cure the curable components of the ink.

Copending Application U.S. Ser. No. 11/289,609, filed concurrently herewith, entitled "Radiation Curable Phase Change Inks Containing Gellants," with the named inventors Peter G. Odell, C. Geoffrey Allen, Christopher A. Wagner, Stephan V. Drappel, Rina Carlini, and Eniko Toma, the disclosure of which is totally incorporated herein by reference, discloses a radiation curable phase change ink preferably used in piezoelectric ink jet devices including an ink vehicle that includes at least one gellant comprising a curable polyamide-epoxy acrylate component and a polyamide component and at least one colorant The use of the gellant enables the ink to form a gel state having a viscosity of at least $10^3$ mPa·s at very low temperatures of about 25° C. to about 100° C. The ink may thus be jetted at very low jelling temperatures of, for example, about 40° C. to about 110° C. The ink may be used to form an image by healing the ink to a first temperature at which the ink may be jetted, jetting onto a member or substrate maintained at a second temperature at which the ink forms a gel state, and exposing the ink to radiation energy to polymerize curable components of the ink.

Copending Application U.S. Ser. No. 11/289,620, filed concurrently herewith, entitled "Phase Change Inks," with the named inventors Peter Gordon Odell, Paul F. Smith, Jennifer Lynne Belelie, Eniko Toma, Stephan Drappel, C. Geoffrey Allen, Rina Carlini, and Christopher A. Wagner, the disclosure of which is totally incorporated herein by reference, discloses a phase change ink having a viscosity of tram about 4 mPa-s to about 50 mPa-s at a first temperature and a viscosity of from $10^4$ mPa-s to about $10^9$ mPa-s at a second lower temperature. The second temperature may be below the first temperature by at least 10° C., but by no more than 50° C. The first temperature may be from about 60° C. to about 110° C. and the second temperature may be from about 20° C. to about 70° C. A curve of $\log_{10}$ viscosity of the phase change ink plotted against temperature in degrees Celsius may have a slope having an absolute value less than 0.02 at the first temperature and have a slope having an absolute value greater than 0.08 for at least a region between the first and second temperatures.

Copending Application U.S. Ser. No. 11/291,592, filed concurrently herewith, entitled "Phase Change Inks and Methods for Making Same," with the named inventors Adela Goredema, Christine F. Bedford. Marcel P. Breton, and Christopher Wagner, the disclosure of which is totally incorporated herein by reference, discloses a phase change ink composition and a method for forming the ink composition. The phase change ink composition comprises (1) an ink carrier comprising (A) a first component which comprises a monoester wax or blend of monoesters having at least one alkyl group comprising at least 10 carbon atoms, and (B) a second component which comprises a polyalkylene wax, and (2) a urea gellant and (3) a colorant.

Copending Application U.S. Ser. No. 11/291,540, filed concurrently herewith, entitled "Ink Carriers Containing Nanoparticles, Phase Change Inks Including Same and Methods for Making Same," with the named inventors Marcel P. Breton, Adela Goredema, Christine E. Bedford, Christopher Wagner. Sandra Gardner, Nan-Xing Hu, and Bruce Goodbrand, the disclosure ot which is totally incorporated herein by reference, discloses an ink carrier and a method for forming same, and a phase change ink including same. The ink carrier comprises a colloidal dispersion of at least one of silica nanoparticles and metal oxide particles. The ink carrier can also include a low melting wax, and a gelling agent. The ink carrier exhibits a substantially uniform distribution of the nanoparticles so that they are discretely distributed therewithin, and are substantially resistant to the aggregation of the nanoparticles distributed therewithin.

Copending Application U.S. Ser. No. 11/291,283, filed concurrently herewith, entitled "Black Inks and Method for Making Same," with the named inventors Marcel P. Breton, Raymond W. Wong, Christine E. Bedford, Christopher Wagner, and Caroline Turek, the disclosure of which is totally incorporated herein by reference, discloses a phase change black ink composition comprising (1) a low polarity ink carrier comprising (A) an ester-terminated polyamide, (B) a Guerbet alcohol or a Guerbet alcohol mixture containing at least one linear alcohol, and (C) a low polarity wax, and (2) a black colorant. The ink carrier can also contain a dispersant. The ink is resistant to aggregation and settling of the black colorant when a standby-mode printer temperature for the ink is not more than about the gel temperature of the ink.

Copending Application U.S. Ser. No. 11/291,315, filed concurrently herewith, entitled "Ink Carriers, Phase Change Inks Including Same and Methods for Making Same," with the named inventors Marcel P. Breton, Adela Goredema, Christine E. Bedford, Christopher Wagner, Stephan Drappel, Caroline Turek, Raymond W. Wong, and Nadia Edun, the disclosure of which is totally incorporated herein by reference, discloses an ink carrier comprising (A) an antioxidant mixture comprising (a) a hindered phenol antioxidant and (b) a hindered amine antioxidant (B) a polyalkylene wax, (C) a functional wax, and (D) an ester-terminated amide. The low polarity ink carrier is substantially resistant to phase separation, has excellent thermal stability, resists autocatalytic degradation of the ink composition and a substantial color shift upon standing, and provides enhanced humidity resistance. This ink carrier can be combined with a colorant to produce an ink composition.

Copending Applicailon U.S. Ser. No. 11/289,552, filed concurrently herewith, entitled "Curable Overcoat for Wax-Based Inks," with the named inventors Jennifer L. Belelie and Peter G. Odell, the disclosure of which is totally incorporated herein by reference, discloses an ink jettable overprint composition including at least one of a polymerizable monomer and/or a polymerizable oligomer; at least one photoinitiator; and at least one wax.

Copending Application U.S. Ser. No. 11/289,615, filed concurrently herewith, entitled "Radiation Curable Ink Containing a Curable Wax," with the named inventors Jennifer Lynne Belelie, Peter Gordon Odell, Christopher A. Wagner, and C. Geoffrey Allen, the disclosure of which is totally incorporated herein by reference, discloses a curable monomer that is liquid at 25° C., a curable wax, and a colorant together forming a radiation curable ink. This ink may be used to form images by providing the radiation curable ink at a first temperature; applying the radiation curable ink to the substrate to form an image, the substrate being at a second temperature, which is below the first temperature; and exposing the radiation curable ink to radiation to cure the ink.

Copending Application U.S. Ser. No. 11/289,521, filed concurrently herewith, entitled "Curable Phase Change Compositions and Methods for Using Such Compositions," with the named inventors Jennifer L. Belelie, Peter G. Odell, Daryl Vanbesien, and Marcel P. Breton, the disclosure of which is totally incorporated herein by reference, discloses a phase change, curable composition comprising curable monomer, photoinitiator that initiates polymerization of the curable monomer, and phase change agent that provides the composition with an increase in viscosity of at least four orders of magnitude, from a first temperature, the first temperature being from 50° C. to 130° C., to a second temperature, the second temperature being from 0° C. to 70° C., wherein the second temperature is at least 10° C. below the first temperature. A coating over an image may be applied by providing a composition comprising curable monomer at a first temperature; applying the composition over the image, the image being at a second temperature; and exposing the composition to radiation to initiate polymerization of the curable monomer. In this process, the composition has a viscosity at the second temperature that is at least four orders of magnitude greater than its viscosity at the first temperature.

Copending Application U.S. Ser. No. 11/289,605, filed concurrently herewith, entitled "Overcoat Compositions, Oil-Based Ink Compositions, and Processes for Ink-Jet Recording Using Overcoat Compositions and Oil-Based Ink Compositions," with the named inventors Gregory J. Kovacs and Marcel P. Breton, the disclosure of which is totally incorporated herein by reference, discloses overcoat compositions including film-forming resins and organic liquids. Overcoat compositions are included in ink sets that also include oil-based ink compositions. Methods for ink-jet printing use oil-based ink compositions and overcoat compositions.

Copending Application U.S. Ser. No. 11/289,573, filed concurrently herewith, entitled "Pre-Treatment Corn positions, Oil-Based Ink Compositions, and Processes for Ink-Jet Recording Using Pre-Treatment Compositions and Oil-Based Ink Compositions," with the named inventors Gregory J. Kovacs and Marcel P. Breton, the disclosure at which is totally incorporated herein by reference, discloses pre-treatment compositions including organic liquids and cross-linking initiators. Pre-treatment compositions are included in ink sets that also include oil-based ink corn positions. Oil-based ink compositions include organic liquids, unsaturated tally materials having terminal polar functional groups, colorants, and metal salts. Methods for ink-jet printing use pre-treatment compositions and oil-based ink compositions.

Copending Application U.S. Ser. No. 11/290,122, filed concurrently herewith, entitled "Curable Amide Gellant Compounds," with the named inventors Eniko Toma, Peter G. Odell, Adela Goredema, and Jennifer L. Belelie, the disclosure of which is totally incorporated herein by reference, discloses a compound ot the formula

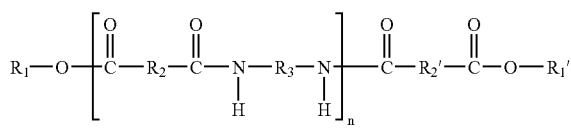

wherein $R_1$ and $R_1'$ each, independently of the other, is an alkyl group having at least one ethylenic unsaturation, an arylalkyl group having at least one ethylenic unsaturation, or an alkylaryl group having at least one ethylenic unsaturation, $R_2$, $R_2'$, and $R_3$ each, independently of the others, are alkylene groups, arylene groups, arylalkylene groups, or alkylarylene groups, and n is an integer representing the number of repeat amide units and is at least 1.

Copending Application U.S. Ser. No. 11/290,121, filed concurrently herewith, entitled "Phase Change Inks Containing Curable Amide Gellant Compounds," with the named inventors Eniko Toma, Jennifer L. Belelie, and Peter G. Odell, the disclosure of which is totally incorporated herein by reference, discloses a phase change ink comprising a colorant an initiator, and a phase change ink carrier, said carrier comprising at least one radically curable monomer compound and a compound of the formula

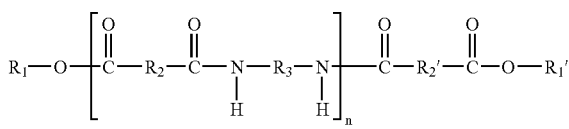

wherein $R_1$ and $R_1'$ each, independently of the other, is an alkyl group having at least one ethylenic unsaturation, an arylalkyl group having at least one ethylenic unsaturation, or an alkylaryl group having at least one ethylenic unsaturation, $R_2$, $R_2'$, and $R_3$ each, independently of the others, are alkylene groups, arylene groups, arylalkylene groups, or alkylarylene groups, and n is an integer representing the number of repeat amide units and is at least 1. Also disclosed herein is a method of printing with the phase change ink.

Copending Application U.S. Ser. No. 11/289,882, filed concurrently herewith, entitled "Process for Making Curable Amide Gellant Compounds," with the named inventors Eniko Toma, Adela Goredema, Jennifer L. Belelie, and Peter G. Odell, the disclosure of which is totally incorporated herein by reference, discloses a process for preparing a compound of the formula

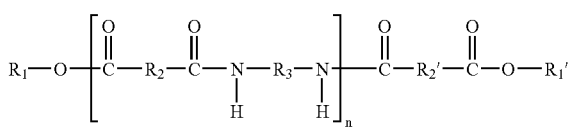

wherein $R_1$ is an alkyl group having at least one ethylenic unsaturation, an arylalkyl group having at least one ethylenic unsaturation, or an alkylaryl group having at least one ethylenic unsaturation, $R_2$ and $R_3$ each, independently of the others, are alkylene groups, arylene groups, arylalkylene groups, or alkylarylene groups, and n is an integer representing the number of repeat amide units and is at least 1, said process comprising: (a) reacting a diacid of the formula

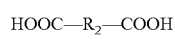

HOOC—$R_2$—COOH with a diamine of the formula

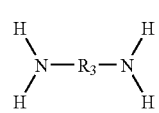

in the presence of a catalyst a solvent and a coupling agent to form an oligoomide intermediate;

and (b) reacting the oligoamide Intermediate with an alcohol of the formula

R₁—OH to form the product.

Copending Application U.S. Ser. No. 11/290,328, filed concurrently herewith, entitled "Method for Preparing Curable Amide Gellant Compounds," with the named inventors Jennifer L. Delelie, Adela Goredema, Peter G. Odell, and Eniko Toma, the disclosure of which is totally incorporated herein by reference, discloses a process for preparing a compound of the formula

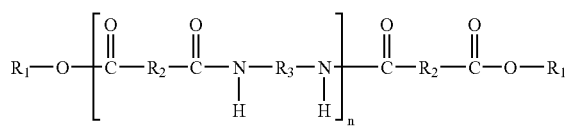

wherein $R_1$ and $R_1'$ each, independently of the other, is an alkyl group having at least one ethylenic unsaturation, an arylalkyl group having at least one ethylenic unsaturation, or an alkylaryl group having at least one ethylenic unsaturation, $R_2$, $R_2'$, and $R_3$ each, independently of the others, are alkylene groups, arylene groups, arylalkylene groups, or alkylarylene groups, and n is an integer representing the number of repeat amide units and is at least 1, said process comprising: (a) reacting a diacid of the formula

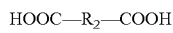
HOOC—R₂—COOH with a diamine of the formula

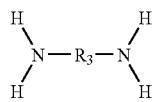

in the absence of a solvent while removing water from the reaction mixture to form an acid-terminated oligoamide intermediate; and (b) reacting the acid-terminated oligoamide intermediate with a monoalcohol of the formula

R₁—OH in the presence of a coupling agent and a catalyst to form the product.

Copending Application U.S. Ser. No. 11/290,202, filed concurrently herewith, entitled "Phase Change Inks Containing Photoinitiator With Phase Change Properties and Gellant Affinity," with the named inventors Peter G. Odell, Eniko Toma, and Jennifer L. Belelie, the disclosure of which is totally incorporated herein by reference, discloses a phase change ink comprising a colorant an initiator, and an ink vehicle, said ink vehicle comprising (a) at least one radically curable monomer compound, and (b) a compound of the formula

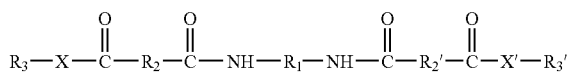

wherein $R_1$ is an alkylene, arylene, arylalkylene, or alkylarylene group, $R_2$ and $R_2'$ each, independently of the other, are alkylene, arylene, arylalkylene, or alkylarylene groups, $R_3$ and $R_3'$ each, independently of the other, are either (a) photoinitiating groups, or (b) groups which are alkyl, aryl, arylalkyl, or alkylaryl groups, provided that at least one of $R_3$ and $R_3'$ is a photoinitiating group, and X and X' each, independently of the other, is an oxygen atom or a group of the formula —NR₄—, wherein $R_4$ is a hydrogen atom, an alkyl group, an aryl group, an arylalkyl group, or an alkylaryl group.

BACKGROUND

Disclosed herein are photoinitiating compounds. More specifically, disclosed herein are photoinitiating compounds particularly compatible with or useful as compositions useful in curable phase change ink compositions. One embodiment is directed to a compound of the formula

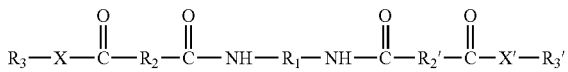

wherein $R_1$ is (i) an alkylene group, including linear and branched, saturated and unsaturated, cyclic and acyclic, and substituted and unsubstituted alkylene groups, and wherein hetero atoms either may or may not be present in the alkylene group, (ii) an arylene group, including substituted and unsubstituted arylene groups, and wherein hetero atoms either may or may not be present in the arylene group, (iii) an arylalkylene group, including substituted and unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, including substituted and unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, including linear and branched, saturated and unsaturated, cyclic and acyclic, and substituted and unsubstituted alkylene groups, and wherein hetero atoms either may or may not be present in the alkylene group, (ii) arylene groups, including substituted and unsubstituted arylene groups, and wherein hetero atoms either may or may not be present in the arylene group, (iii) arylalkylene groups, including substituted and unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, including substituted and unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, including linear and branched, saturated and unsaturated, cyclic and acyclic, and substituted and unsubstituted alkyl groups, and wherein hetero atoms either may or may not be present in the alkyl group, (ii) aryl groups, including substituted and unsubstituted aryl groups, wherein hetero atoms either may or may not be present in the aryl group, (iii) arylalkyl groups, including substituted and unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, including substituted and unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is an oxygen atom or a group of the formula —$NR_4$—, wherein $R_4$ is (i) a hydrogen atom, (ii) an alkyl group, including linear and branched, saturated and unsaturated, cyclic and acyclic, and substituted and unsubstituted alkyl groups, and wherein hetero atoms either may or may not be present in the alkyl group, (iii) an aryl group, including substituted and unsubstituted aryl groups, and wherein hetero atoms either may or may not be present in the aryl group, (iv) an arylalkyl group, including substituted and unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, including substituted and unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 5,804,671 (Dones et al.), the disclosure of which is totally incorporated herein by reference, discloses a composition that is useful in the preparation of radiation curable coatings. The composition comprises the reaction product of an epoxy component comprising a diepoxide and an acid component comprising an ethylenically unsaturated carboxylic acid or reactive derivative thereof, reacted in the presence of a polyamide based on a polymerized fatty acid. The polyamide preferably has a number average molecular weight of less than about 10,000 g/mole. Also provided is a polymerizable composition comprising the reaction product and a reactive diluent. A method of coating a substrate is also provided which comprises applying to a substrate a composition comprising the reaction product and exposing said composition to radiation to cure said composition.

U.S. Pat. No. 5,889,076 (Dones et al.), the disclosure of which is totally incorporated herein by reference, discloses a composition that is useful in the preparation of radiation curable coatings. The composition comprises the reaction product of an epoxy component and an acid component comprising an ethylenically unsaturated carboxylic acid or reactive derivative thereof, reacted in the presence of, or post-reaction blended with, a polyamide based on a polymerized fatty acid. The polyamide preferably has a number average molecular weight of less than about 10,000 g/mole. Also provided is a polymerizable composition comprising the reaction product, the polyamide, and a reactive diluent.

A method of coating a substrate is also provided which comprises applying to a substrate a composition comprising the reaction product and the polyamide and exposing said composition to radiation to cure said composition.

U.S. Pat. No. 6,239,189 (Narayan et al.), the disclosure of which is totally incorporated herein by reference, discloses a radiation-polymerizable composition containing at least one radiation curable acrylate resin oligomer prepared by reacting an alkoxylated polyol with a first acid component which includes an ethylenically unsaturated carboxylic acid, and a rheology modifier prepared by reacting a diepoxide with a second acid component which includes an ethylenically unsaturated carboxylic acid or reactive derivative thereof in the presence of a polyamide based on a polymerized fatty acid. The ethylenically unsaturated carboxylic acids of the first and second acid components are preferably acrylic acid or methacrylic acids. The diepoxide is preferably a diglycidyl ether such as bisphenol A. Colorants such as pigments or dyes optionally may be incorporated into the composition to form a printing ink which is curable by ultraviolet (UV) or electron beam radiation.

U.S. Pat. No. 6,316,517 (Dones et al.), the disclosure of which is totally incorporated herein by reference, discloses radiation-polymerizable compositions especially useful as or in a flush vehicle for making flushed pigments. The compositions contain at least one radiation-curable acrylated resin component and a copolymerizable rheology modifier component.

U.S. Patent Publication 2003/0036587 (Kozak), the disclosure of which is totally incorporated herein by reference, discloses rheology-controlled epoxy-based compositions particularly well suited for use in coating applications such as in the assembly of ink jet printheads for the printing industry, and in the microelectronics industry such as in the assembly of semiconductor devices.

U.S. Pat. No. 6,586,492 (Caiger et al.), the disclosure of which is totally incorporated herein by reference, discloses an ink-jet ink including an ink jet vehicle and a colorant. The vehicle includes at least 35 percent by weight radiation curable material based on the total vehicle weight. The vehicle may but does not necessarily include a thickener. The vehicle is a paste or a solid at 20° C. and has a viscosity of less than 25 centipoise between 40° C. and 130° C.

U.S. Pat. No. 6,467,897 (Wu et al.), the disclosure of which is totally incorporated herein by reference, discloses compositions that incorporate surface modified, nanometer sized, inorganic oxide particles into energy curable fluids. The surface modification aspect allows the compatibility between the particles and fluid to be controllably adjusted to achieve a wide range of rheological characteristics. For printing, preferred compositions have favorable dot gain and thickness build up. When the composition is cured, the presence of the particles also helps improve physical properties such as hardness, modulus, abrasion resistance, refractive index, and the like. The compositions are particularly well-suited for forming printed, radiation cured features on substrates such as paper, signs, walkways, roadways, motor vehicles, boats, aircraft, furniture, equipment, and the like.

U.S. Pat. No. 6,896,937 (Woudenberg), the disclosure of which is totally incorporated herein by reference, discloses radiation-curable ink compositions and methods of printing including the compositions. In some embodiments, a radiation-curable hot melt ink composition includes a colorant, a polymerizable monomer, and a photoinitiating system. The photoinitiating system can include 0.5 to 1.5 percent by weight of an aromatic ketone photoinitiator, 2 to 10 percent by weight of an amine synergist, 3 to 8 percent by weight of an alpha-cleavage type photoinitiator, and 0.5 to 1.5 percent by weight of a photosensitizer.

While known compositions and processes are suitable for their intended purposes, a need remains for improved photoinitiators. In addition, a need remains for improved phase change inks. Further, a need remains for photoinitiators that are soluble in, miscible in, or otherwise compatible with phase change ink vehicles. Additionally, a need remains for photoinitiators that lead to reduced odor when used in curable phase change inks prior to curing. There is also a need for photoinitiators that lead to reduced odor when used in curable phase change inks subsequent to curing. In addition, there is a need for photoinitiators that lead to reduced surface yellowing in images when used in curable phase change inks. Further, there is a need for photoinitiators that exhibit reduced migration through cured images when used in curable phase change inks. Additionally, there is a need for photoinitiators having improved affinity for phase change inks exhibiting a gel phase during the printing process. A need also remains for a photoinitiator having reduced volatility in itself and also having reduced volatility of its fragments. In addition, a need remains for photoinitiators that in themselves exhibit gellant characteristics. Further, a need remains for photoinitiators that have improved affinity for the ordered microstructure of the gel phase, as opposed to being excluded from that order. Additionally, a need remains for photoinitiators that are themselves curable.

SUMMARY

Disclosed herein is a compound of the formula

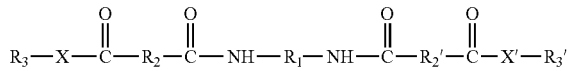

wherein $R_1$ is (i) an alkylene group, including linear and branched, saturated and unsaturated, cyclic and acyclic, and substituted and unsubstituted alkylene groups, and wherein hetero atoms either may or may not be present in the alkylene group, (ii) an arylene group, including substituted and unsubstituted arylene groups, and wherein hetero atoms either may or may not be present in the arylene group, (iii) an arylalkylene group, including substituted and unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, including substituted and unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, including linear and branched, saturated and unsaturated, cyclic and acyclic, and substituted and unsubstituted alkylene groups, and wherein hetero atoms either may or may not be present in the alkylene group, (ii) arylene groups, including substituted and unsubstituted arylene groups, and wherein hetero atoms either may or may not be present in the arylene group, (iii) arylalkylene groups, including substituted and unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, including substituted and unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, R$_3$ and R$_3$' each, independently of the other, are either (a) photoinitiating groups, or (b) groups which are (i) alkyl groups, including linear and branched, saturated and unsaturated, cyclic and acyclic, and substituted and unsubstituted alkyl groups, and wherein hetero atoms either may or may not be present in the alkyl group, (ii) aryl groups, including substituted and unsubstituted aryl groups, wherein hetero atoms either may or may not be present in the aryl group, (iii) arylalkyl groups, including substituted and unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, including substituted and unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of R$_3$ and R$_3$' is a photoinitiating group, and X and X' each, independently of the other, is an oxygen atom or a group of the formula —NR$_4$—, wherein R$_4$ is (i) a hydrogen atom, (ii) an alkyl group, including linear and branched, saturated and unsaturated, cyclic and acyclic, and substituted and unsubstituted alkyl groups, and wherein hetero atoms either may or may not be present in the alkyl group, (iii) an aryl group, including substituted and unsubstituted aryl groups, and wherein hetero atoms either may or may not be present in the aryl group, (iv) an arylalkyl group, including substituted and unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, including substituted and unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group.

DETAILED DESCRIPTION

Disclosed herein are compounds of the formula

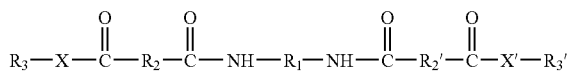

wherein:

R$_1$ is:

(i) an alkylene group (wherein an alkylene group is defined as a divalent aliphatic group or alkyl group, including linear and branched, saturated and unsaturated, cyclic and acyclic, and substituted and unsubstituted alkylene groups, and wherein hetero atoms, such as oxygen, nitrogen, sulfur, silicon, phosphorus, boron, and the like either may or may not be present in the alkylene group), in one embodiment with at least 1 carbon atom, and in one embodiment with no more than about 12 carbon atoms, in another embodiment with no more than about 4 carbon atoms, and in yet another embodiment with no more than about 2 carbon atoms, although the number of carbon atoms can be outside of these ranges, (ii) an arylene group (wherein an arylene group is defined as a divalent aromatic group or aryl group, including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 14 carbon atoms, in another embodiment with no more than about 10 carbon atoms, and in yet another embodiment with no more than about 6 carbon atoms, although the number of carbon atoms can be outside of these ranges, (iii) an arylalkylene group (wherein an arylalkylene group is defined as a divalent arylalkyl group, including substituted and unsubstituted arylalkylene groups, wherein the alkyl portion of the arylalkylene group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 32 carbon atoms, in another embodiment with no more than about 22 carbon atoms, and in yet another embodiment with no more than about 7 carbon atoms, although the number of carbon atoms can be outside of these ranges, or (iv) an alkylarylene group (wherein an alkylarylene group is defined as a divalent alkylaryl group, including substituted and unsubstituted alkylarylene groups, wherein the alkyl portion of the alkylarylene group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 32 carbon atoms, in another embodiment with no more than about 22 carbon atoms, and in yet another embodiment with no more than about 7 carbon atoms, although the number of carbon atoms can be outside of these ranges, wherein the substituents on the substituted alkylene, arylene, arylalkylene, and alkylarylene groups can be (but are not limited to) halogen atoms, cyano groups, pyridine groups, pyridinium groups, ether groups, aldehyde groups, ketone groups, ester groups, amide groups, carbonyl groups, thiocarbonyl groups, sulfide groups, nitro groups, nitroso groups, acyl groups, azo groups, urethane groups, urea groups, mixtures thereof, and the like, wherein two or more substituents can be joined together to form a ring;

R$_2$ and R$_2$' each, independently of the other, are:

(i) alkylene groups (wherein an alkylene group is defined as a divalent aliphatic group or alkyl group, including linear and branched, saturated and unsaturated, cyclic and acyclic, and substituted and unsubstituted alkylene groups, and wherein hetero atoms, such as oxygen, nitrogen, sulfur, silicon, phosphorus, boron, and the like either may or may not be present in the alkylene group), in one embodiment with at least 1 carbon atom, and in one embodiment with no more than about 54 carbon atoms, and in another embodiment with no more than about 36 carbon atoms, although the number of carbon atoms can be outside of these ranges, (ii) arylene groups (wherein an arylene group is defined as a divalent aromatic group or aryl group, including substituted and unsubstituted arylene groups, and wherein hetero atoms, such as oxygen, nitrogen, sulfur, silicon, phosphorus, boron, and the like either may or may not be present in the arylene group), in one embodiment with at least about 5 carbon atoms, and in another embodiment with at least about 6 carbon atoms, and in one embodiment with no more than about 14 carbon atoms, in another embodiment with no more than about 10 carbon atoms, and in yet another embodiment with no more than about 7 carbon atoms, although the number of carbon atoms can be outside of these ranges, (iii) arylalkylene groups (wherein an arylalkylene group is defined as a divalent arylalkyl group, including substituted and unsubstituted arylalkylene groups, wherein the alkyl portion of the arylalkylene group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the arylalkylene group), in one embodiment with at least about 6 carbon atoms, and in another embodiment with at least about 7 carbon atoms, and in one embodiment with no more than about 32 carbon atoms, in another embodiment with no more than about 22 carbon atoms, and in yet another embodiment with no more than about 8 carbon atoms, although the number of carbon atoms can be outside of these ranges, or (iv) alkylarylene groups (wherein an alkylarylene group is defined as a divalent alkylaryl group, including substituted and unsubstituted alkylarylene groups, wherein the alkyl portion of the alkylarylene group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the alkylarylene group), in one embodiment with at least about 6 carbon atoms, and in another embodiment with at least about 7 carbon atoms, and in one embodiment with no more than about 32 carbon atoms, in another embodiment with no more than about 22 carbon atoms, and in yet another embodiment with no more than about 7 carbon atoms, although the number of carbon atoms can be outside of these ranges, wherein the substituents on the substituted alkylene, arylene, arylalkylene, and alkylarylene groups can be (but are not limited to) halogen atoms, cyano groups, ether groups, aldehyde groups, ketone groups, ester groups, amide groups, carbonyl groups, thiocarbonyl groups, phosphine groups, phosphonium groups, phosphate groups, nitrile groups, mercapto groups, nitro groups, nitroso groups, acyl groups, acid anhydride groups, azide groups, azo groups, cyanato groups, urethane groups, urea groups, mixtures thereof, and the like, wherein two or more substituents can be joined together to form a ring;

$R_3$ and $R_3'$ each, independently of the other, are either:

(a) photoinitiating groups, such as groups derived from 1-(4-(2-hydroxyethoxy)phenyl)-2-hydroxy-2-methylpropan-1-one, of the formula

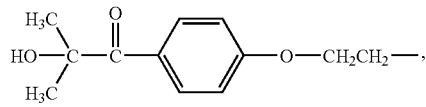

groups derived from 1-hydroxycyclohexylphenylketone, of the formula

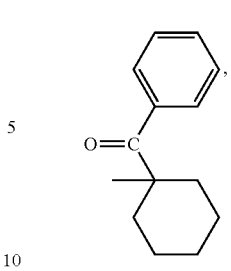

groups derived from 2-hydroxy-2-methyl-1-phenylpropan-1-one, of the formula

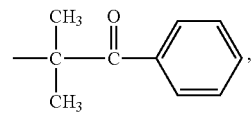

groups derived from N,N-dimethylethanolamine or N,N-dimethylethylenediamine, of the formula

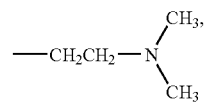

or the like, or:

(b) a group which is:

(i) an alkyl group (including linear and branched, saturated and unsaturated, cyclic and acyclic, and substituted and unsubstituted alkyl groups, and wherein hetero atoms, such as oxygen, nitrogen, sulfur, silicon, phosphorus, boron, and the like either may or may not be present in the alkyl group), in one embodiment with at least about 2 carbon atoms, in another embodiment with at least about 3 carbon atoms, and in yet another embodiment with at least about 4 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, (ii) an aryl group (including substituted and unsubstituted aryl groups, and wherein hetero atoms, such as oxygen, nitrogen, sulfur, silicon, phosphorus, boron, and the like either may or may not be present in the aryl group), in one embodiment with at least about 5 carbon atoms, and in another embodiment with at least about 6 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as phenyl or the like, (iii) an arylalkyl group (including substituted and unsubstituted arylalkyl groups, wherein the alkyl portion of the arylalkyl group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the arylalkyl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as benzyl or the like, or (iv) an alkylaryl group (including substituted and unsubstituted alkylaryl groups, wherein the alkyl portion of the alkylaryl group can be linear or branched, saturated or unsaturated, and cyclic or acyclic, and wherein hetero atoms, such as oxygen, nitrogen, sulfur, silicon, phosphorus, boron, and the like either may or may not be present in either the aryl or the alkyl portion of the alkylaryl group), in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, such as tolyl or the like, wherein the substituents on the substituted alkyl, arylalkyl, and alkylaryl groups can be (but are not limited to) halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring;

provided that at least one of $R_3$ and $R_3'$ is a photoinitiating group;

and X and X' each, independently of the other, is an oxygen atom or a group of the formula —$NR_4$—, wherein $R_4$ is:

(i) a hydrogen atom;

(ii) an alkyl group, including linear and branched, saturated and unsaturated, cyclic and acyclic, and substituted and unsubstituted alkyl groups, and wherein hetero atoms either may or may not be present in the alkyl group, in one embodiment with at least 1 carbon atom, and in one embodiment with no more than about 100 carbon atoms, in another embodiment with no more than about 60 carbon atoms, and in yet another embodiment with no more than about 30 carbon atoms, although the number of carbon atoms can be outside of these ranges, (iii) an aryl group, including substituted and unsubstituted aryl groups, and wherein hetero atoms either may or may not be present in the aryl group, in one embodiment with at least about 5 carbon atoms, and in another embodiment with at least about 6 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, (iv) an arylalkyl group, including substituted and unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, or (v) an alkylaryl group, including substituted and unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, in one embodiment with at least about 6 carbon atoms, and in another embodiment with at least about 7 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, wherein the substituents on the substituted alkyl, aryl, arylalkyl, and alkylaryl groups can be (but are not limited to) halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring.

In one specific embodiment, $R_2$ and $R_2'$ are the same as each other; in another specific embodiment, $R_2$ and $R_2'$ are different from each other. In one specific embodiment, $R_3$ and $R_3'$ are the same as each other; in another specific embodiment, $R_3$ and $R_3'$ are different from each other.

In one specific embodiment, $R_2$ and $R_2'$ are each groups of the formula —$C_{34}H_{56+a}$— and are branched alkylene groups which may include unsaturations and cyclic groups, wherein a is an integer of 0, 1, 2, 3, 4, 5, 6, 7, 8, 9, 10, 11, or 12, including (but not limited to) isomers of the formula

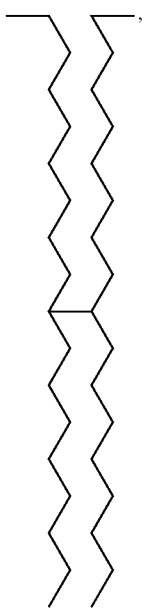

In one specific embodiment, $R_1$ is an ethylene (—$CH_2CH_2$—) group.

In one specific embodiment, $R_3$ and $R_3'$ are both

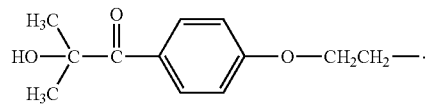

In one specific embodiment, the compound is of the formula

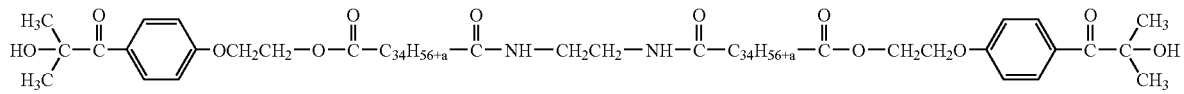

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

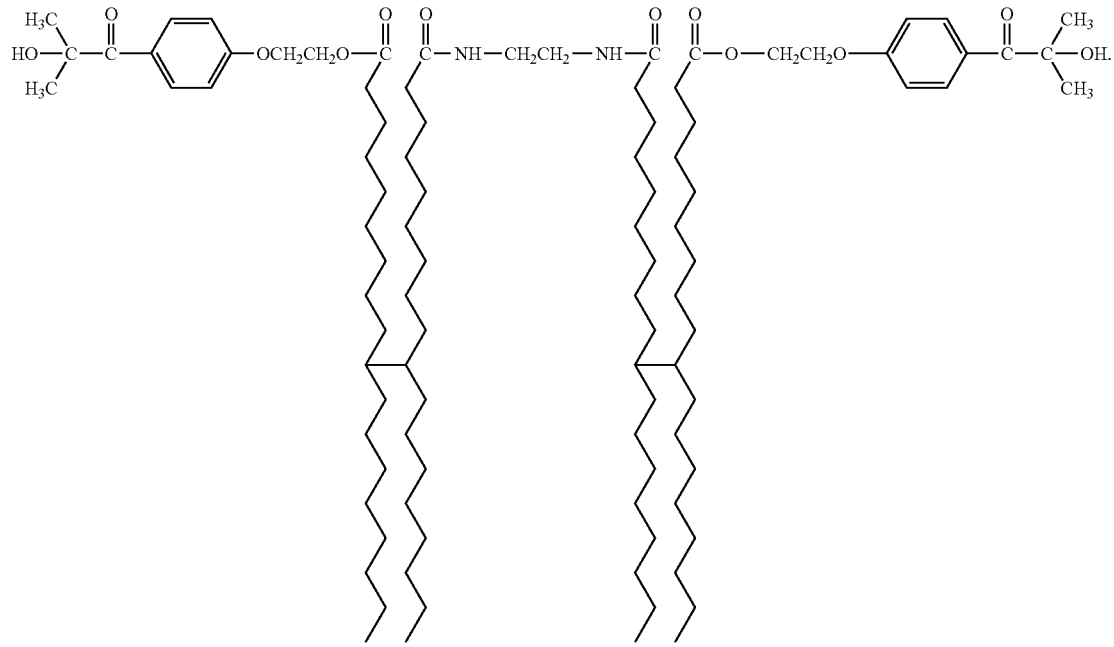

Additional specific examples of compounds of this formula include those of the formula

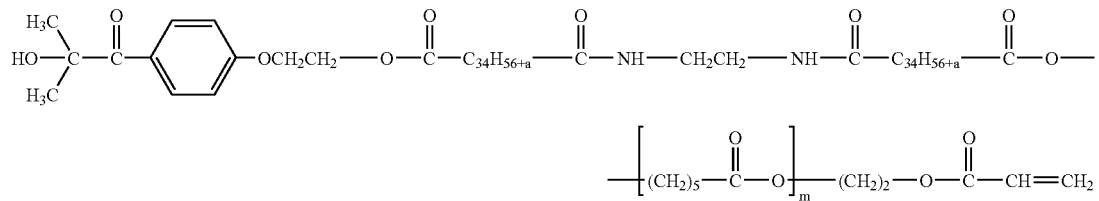

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and wherein m is an integer, including but not limited to embodiments wherein m is 2, including (but not limited to) isomers of the formula

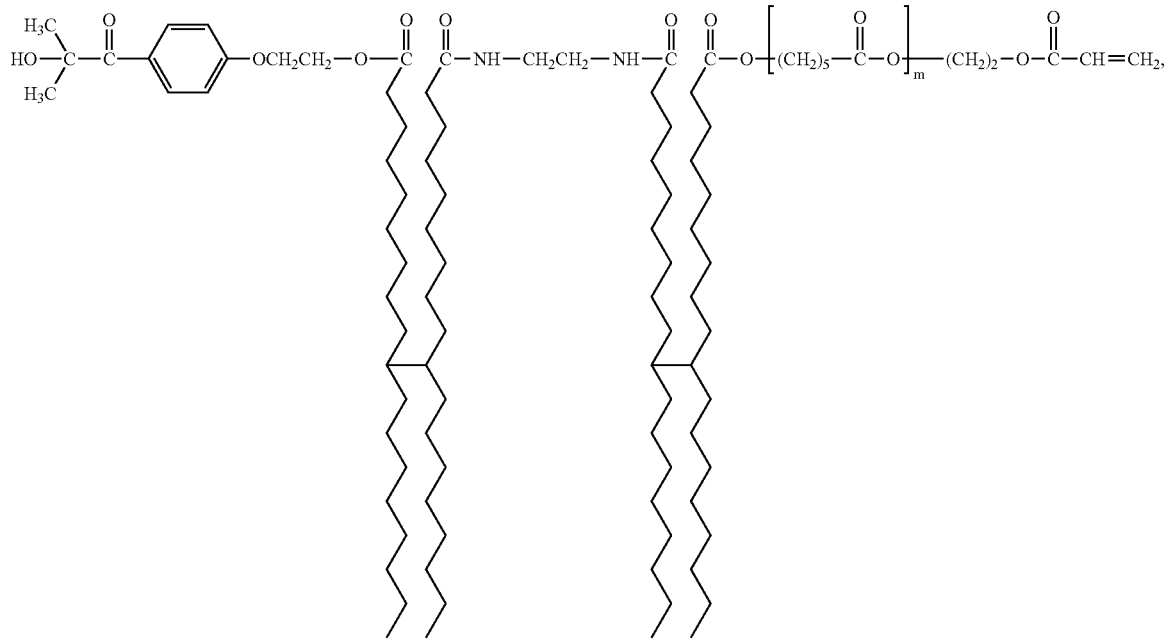

those of the formula

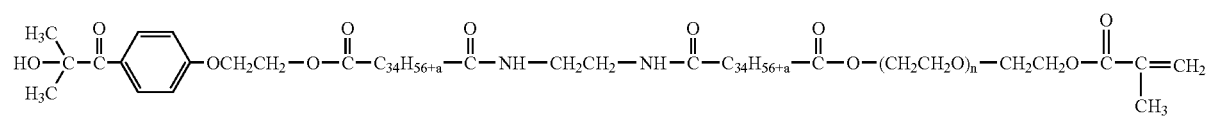

wherein —$C_{34}H_{56+a}$— represents a branched alkylene group which may include unsaturations and cyclic groups, wherein a is an integer of 0 1, 2, 3, 4, 5, 6, 7, 8, 9, 10, 11, or 12 and wherein n is an integer, including but not limited to embodiments wherein n is 2 and wherein n is 5, including (but not limited to) isomers of the formula

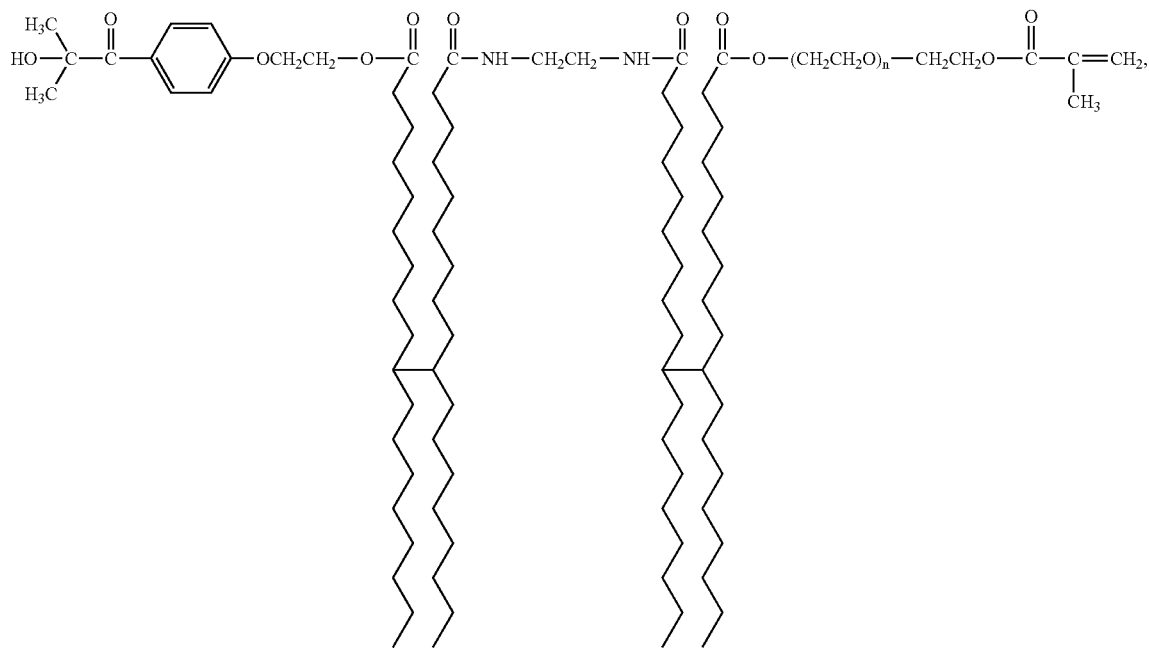

those of the formula

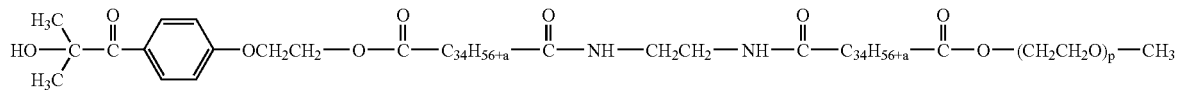

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and wherein p is an integer, including but not limited to embodiments wherein p is 2 and wherein p is 3, including (but not limited to) isomers of the formula

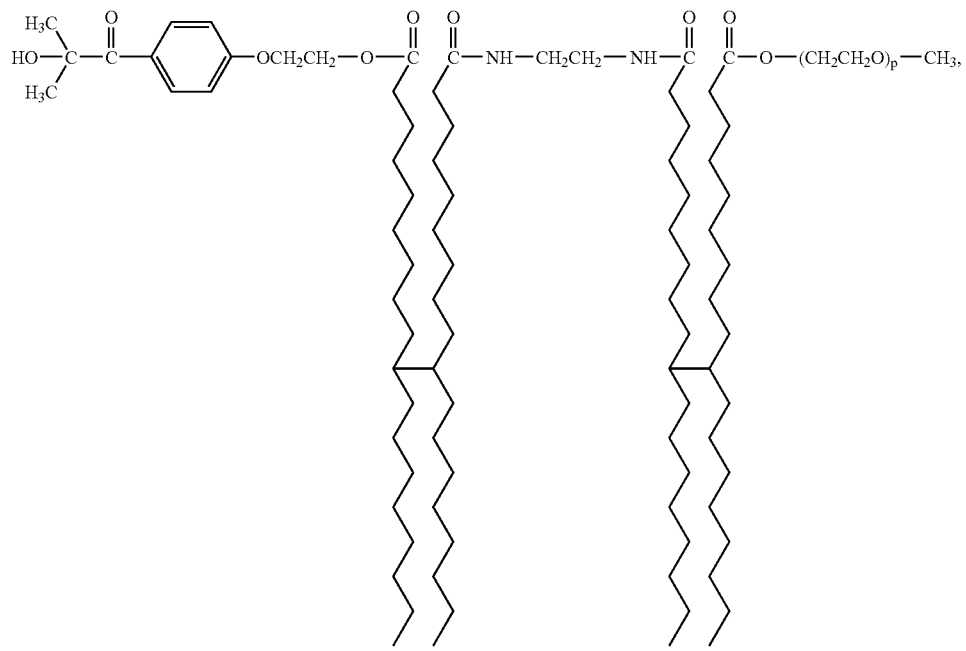

those of the formula

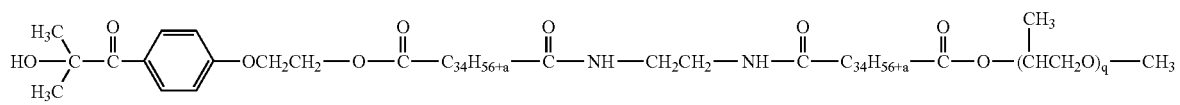

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and wherein q is an integer, including but not limited to embodiments wherein q is 2 and wherein q is 3, including (but not limited to) isomers of the formula

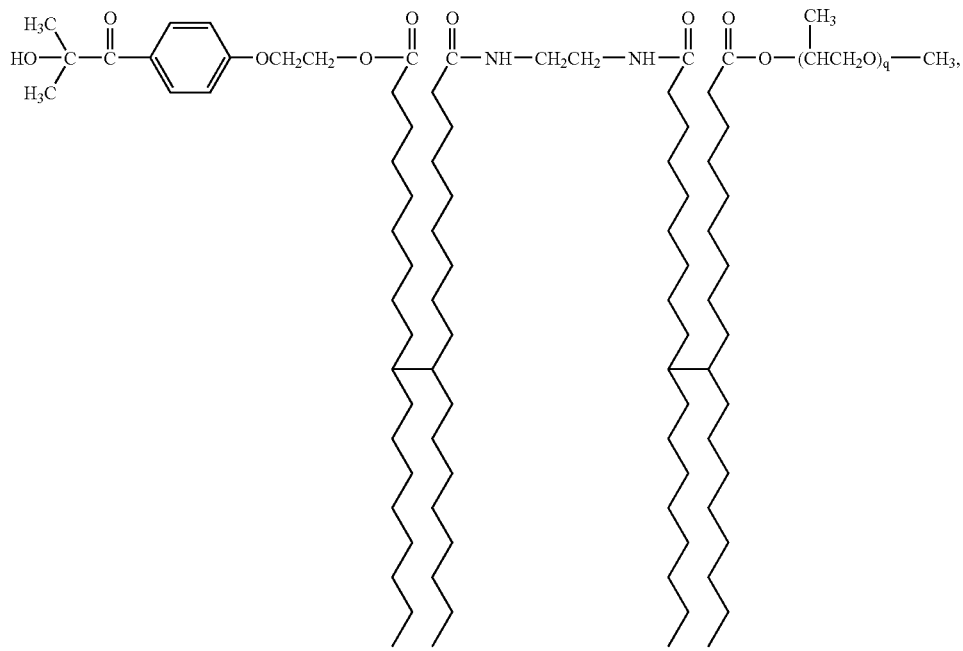
those of the formula
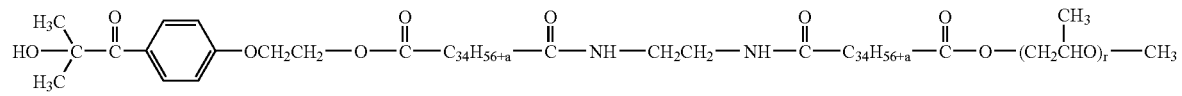
wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 and wherein r is an integer, including but not limited to embodiments wherein r is 2 and wherein r is 3, including (but not limited to) isomers of the formula
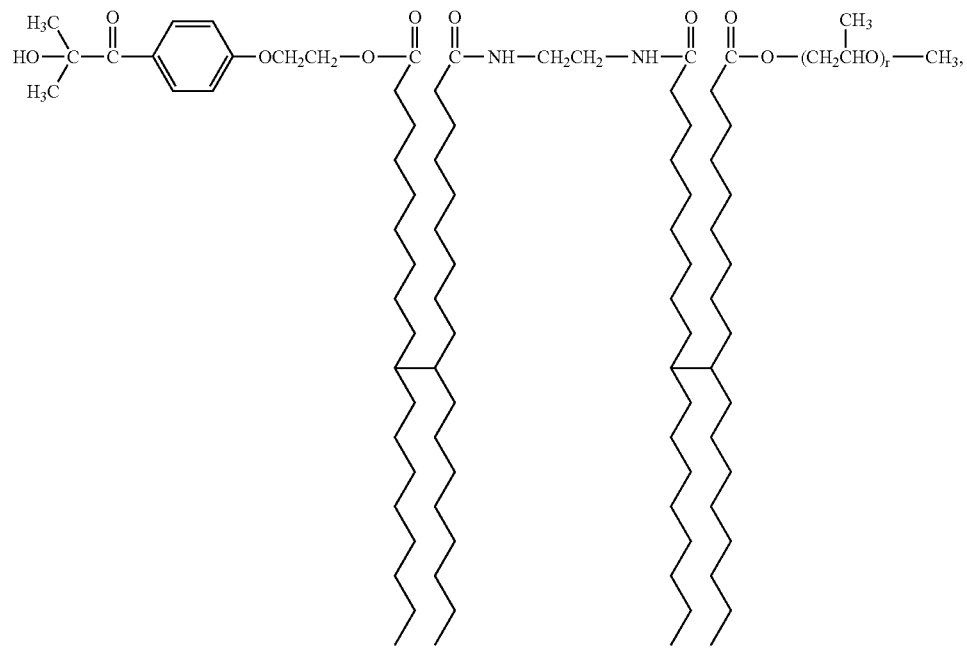
and the like, as well as mixtures thereof.

Compounds as disclosed herein can be prepared by any desired or effective method. For example, in one specific embodiment, about two molar equivalents of a diacid of the formula

HOOC—R$_2$—COOH about one molar equivalent of a diamine of the formula

H$_2$N—R$_1$—NH$_2$ and about two molar equivalents of a monoalcohol of the formula

R$_3$—OH can be reacted by use of the coupling agent such as 1,3-dicyclohexylcarbodiimide (DCC) in the presence of a catalyst such as 4-dimethylaminopyridine (DMAP), in the presence of an optional solvent such as methylene chloride (CH$_2$Cl$_2$). The ingredients can be mixed together and a one-pot reaction can be employed. More specifically, the diacid, the diamine, and the dicyclohexylcarbodiimide can be mixed together in a first step, and the monoalcohol can be added to the reaction mixture in a second step. The reaction proceeds as follows:

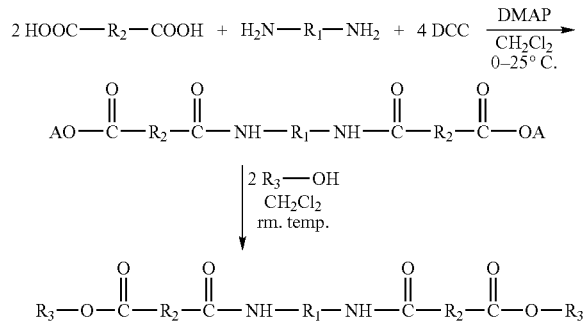

wherein A is the coupling agent.

The diacid and the diamine are present in any desired or effective relative amounts, in one embodiment at least about 0.4 mole of diamine per every 1 mole of diacid, in another embodiment at least about 0.45 mole of diamine per every 1 mole of diacid, and in yet another embodiment at least about 0.5 mole of diamine per every one mole of diacid, and in one embodiment no more than about 0.57 mole of diamine per every 1 mole of diacid, in another embodiment no more than about 0.53 mole of diamine per every 1 mole of diacid, and in yet another embodiment no more than about 0.51 mole of diamine per every 1 mole of diacid, although the relative amounts can be outside of these ranges.

The diacid and the monoalcohol are present in any desired or effective relative amounts, in one embodiment at least about 0.75 mole of monoalcohol per every 1 mole of diacid, in another embodiment at least about 0.9 mole of monoalcohol per every 1 mole of diacid, and in yet another embodiment at least about 1 mole of monoalcohol per every one mole of diacid, and in one embodiment no more than about 1.5 moles of monoalcohol per every 1 mole of diacid, in another embodiment no more than about 1.4 moles of monoalcohol per every 1 mole of diacid, and in yet another embodiment no more than about 1.25 moles of monoalcohol per every 1 mole of diacid, although the relative amounts can be outside of these ranges.

The diamine and the monoalcohol are present in any desired or effective relative amounts, in one embodiment at least about 1.5 moles of monoalcohol per every 1 mole of diamine, in another embodiment at least about 1.75 moles of monoalcohol per every 1 mole of diamine, and in yet another embodiment at least about 2 moles of monoalcohol per every one mole of diamine, and in one embodiment no more than about 2.5 moles of monoalcohol per every 1 mole of diamine, in another embodiment no more than about 2.4 moles of monoalcohol per every 1 mole of diamine, and in yet another embodiment no more than about 2.25 moles of monoalcohol per every 1 mole of diamine, although the relative amounts can be outside of these ranges.

Examples of suitable coupling agents include 1,3-dicyclohexylcarbodiimide (DCC), of the formula

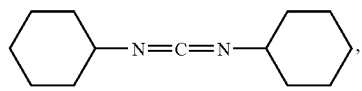

1-(3-(dimethylamino)propyl) 3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate (BOP), (o-benzotriazol-1-yl)-N,N,N', N'-bis(tetramethylene)uronium hexafluorophosphate (HBTU), bis(2-oxo-3-oxazolidinyl)phosphonic chloride (BOP-Cl), (1H-1,2,3-benzotriazol-1-yloxy)tris(pyrrolidino) phosphonium hexafluorophosphate (PyBOP), and the like, as well as mixtures thereof.

The coupling agent and the diacid are present in any desired or effective relative amounts, in one embodiment at least about 0.4 mole of diacid per every 1 mole of coupling agent, in another embodiment at least about 0.45 mole of diacid per every 1 mole of coupling agent, and in yet another embodiment at least about 0.5 mole of diacid per every one mole of coupling agent, and in one embodiment no more than about 0.57 mole of diacid per every 1 mole of coupling agent, in another embodiment no more than about 0.53 mole of diacid per every 1 mole of coupling agent, and in yet another embodiment no more than about 0.51 mole of diacid per every 1 mole of coupling agent, although the relative amounts can be outside of these ranges.

Examples of suitable catalysts include 4-dimethylaminopyridine (DMAP), of the formula

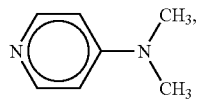

triethylamine, 1,8-diazabicyclo(5.4.0)undec-7-ene (DBU), and the like, as well as mixtures thereof.

The catalyst and the diacid are present in any desired or effective relative amounts, in one embodiment at least about 0.05 mole of catalyst per every 1 mole of diacid, in another embodiment at least about 0.1 mole of catalyst per every 1 mole of diacid, and in yet another embodiment at least about 0.2 mole of catalyst per every one mole of diacid, and in one embodiment no more than about 1 mole of catalyst per every 1 mole of diacid, in another embodiment no more than about 0.8 mole of catalyst per every 1 mole of diacid, and in yet another embodiment no more than about 0.5 mole of catalyst per every 1 mole of diacid, although the relative amounts can be outside of these ranges.

When the optional solvent is employed, any desired or effective solvent can be employed. Examples of suitable solvents include methylene chloride, tetrahydrofuran, methyl ethyl ketone, toluene, dimethyl formamide, diethyl ether, hexane, ethyl acetate, and the like, as well as mixtures thereof, When the optional solvent is employed, the solvent can be present in any desired or effective amount, in one embodiment at least about 30 grams of diacid per liter of solvent, in another embodiment at least about 40 grams of diacid per liter of solvent, and in yet another embodiment at least about 50 grams of diacid per liter of solvent, and in one embodiment no more than about 150 grams of diacid per liter of solvent, in another embodiment no more than about 125 grams of diacid per liter of solvent, and in yet another embodiment no more than about 100 grams of diacid per liter of solvent, although the amount of solvent can be outside of these ranges.

The reaction between the diacid and the diamine in the first step of the reaction can be carried out at any desired or effective temperature, in one embodiment at least about −5° C., in another embodiment at least about −2.5° C., and in yet another embodiment at least about 0° C., and one embodiment no more than about 5° C., in another embodiment no more than about 3° C., and in yet another embodiment no more than about 2° C., although the temperature can be outside of these ranges. Thereafter, the reaction product of the diacid and diamine can be reacted with the monoalcohol at any desired or effective temperature, in one embodiment at least about 15° C., in another embodiment at least about 20° C., and in yet another embodiment at least about 25° C., and one embodiment no more than about 35° C., in another embodiment no more than about 30° C., and in yet another embodiment no more than about 27° C., although the temperature can be outside of these ranges.

The reaction between the diacid, the diamine, and the monoalcohol can be carried out for any desired or effective period of time, in one embodiment at least about 3.5 hours, in another embodiment at least about 4 hours, and in yet another embodiment at least about 4.5 hours, and in one embodiment no more than about 6.5 hours, in another embodiment no more than about 6 hours, and in another embodiment no more than about 5 hours, although the period of time can be outside of these ranges.

Subsequent to completion of the reaction, the product can be isolated by filtration of any solid by-products, or by washing the solution with water depending on the activating agent used. The solvent can be removed by rotary evaporation. If needed, the product can be purified by washing with acetone and drying.

Compounds as disclosed herein can also be prepared by first reacting about two molar equivalents of a diacid of the formula

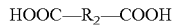

and about one molar equivalent of a diamine of the formula

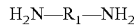

under neat conditions (i.e., in the absence of a solvent) at elevated temperatures while removing water from the reaction mixture to form an acid-terminated oligoamide of the formula

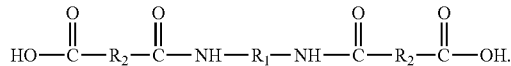

Thereafter, the acid-terminated oligoamide thus formed can be reacted with about 2 molar equivalents of a monoalcohol of the formula $R_3$—OH by use of a coupling agent such as 1,3-dicyclohexylcarbodiimide (DCC) in the presence of a catalyst such as 4-dimethylaminopyridine (DMAP) in the presence of a solvent such as methylene chloride ($CH_2Cl_2$) at reduced temperatures. The reaction proceeds as follows:

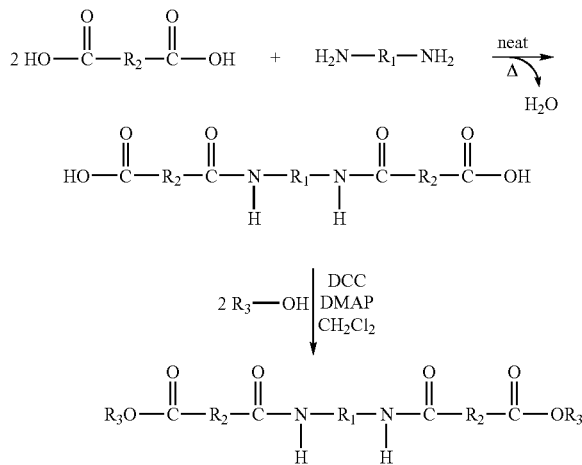

The diacid and the diamine are present in any desired or effective relative amounts, in one embodiment at least about 0.75 mole of diamine per every 2 moles of diacid, in another embodiment at least about 0.85 mole of diamine per every 2 moles of diacid, and in yet another embodiment at least about 1 mole of diamine per every 2 moles of diacid, and in one embodiment no more than about 1.5 moles of diamine per every 2 moles of diacid, in another embodiment no more than about 1.35 moles of diamine per every 2 moles of diacid, and in yet another embodiment no more than about 1.25 moles of diamine per every 2 moles of diacid, although the relative amounts can be outside of these ranges.

Water can be removed from the reaction mixture between the diacid and the diamine by any desired or effective method, such as by a Dean-Stark trap, molecular sieves or other drying agents, or the like.

The reaction between the diacid and the diamine generally is run neat, i.e., in the absence of a solvent, although a solvent can be used if desired.

The reaction between the diacid and the diamine can be carried out at any desired or effective temperature, in one embodiment at least about 130° C., in another embodiment at least about 140° C., and in yet another embodiment at least about 155° C., and one embodiment no more than about 180° C., in another embodiment no more than about 175° C., and in yet another embodiment no more than about 165° C., although the temperature can be outside of these ranges.

The reaction between the diacid and the diamine can be carried out for any desired or effective period of time, in one embodiment at least about 2 hours, in another embodiment at least about 2.5 hours, and in yet another embodiment at least about 3 hours, and in one embodiment no more than about 5 hours, in another embodiment no more than about 4.5 hours, and in another embodiment no more than about 4 hours, although the period of time can be outside of these ranges.

Thereafter, the acid-terminated oligoamide intermediate and the monoalcohol are reacted in the presence of a coupling agent, a catalyst, and a solvent.

Examples of suitable coupling agents include 1,3-dicyclohexylcarbodiimide (DCC), of the formula

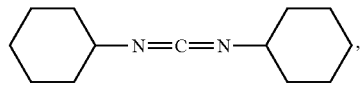

1-(3-(dimethylamino)propyl) 3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate (BOP), (o-benzotriazol-1-yl)-N,N,N',N'-bis(tetramethylene)uronium hexafluorophosphate (HBTU), bis(2-oxo-3-oxazolidinyl)phosphonic chloride (BOP-Cl), (1H-1,2,3-benzotriazol-1-yloxy)tris(pyrrolidino) phosphonium hexafluorophosphate (PyBOP), and the like, as well as mixtures thereof.

Examples of suitable catalysts include 4-dimethylaminopyridine (DMAP), of the formula

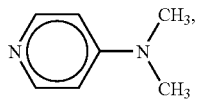

triethylamine, 1,8-diazabicyclo(5.4.0)undec-7-ene (DBU), and the like, as well as mixtures thereof.

The acid-terminated oligoamide intermediate and the monoalcohol are present in any desired or effective relative amounts, in one embodiment at least about 2 moles of monoalcohol per every 1 mole of acid-terminated oligoamide intermediate, in another embodiment at least about 2.15 moles of monoalcohol per every 1 mole of acid-terminated oligoamide intermediate, and in yet another embodiment at least about 2.25 moles of monoalcohol per every one mole of acid-terminated oligoamide-intermediate, and in one embodiment no more than about 2.75 moles of monoalcohol per every 1 mole of acid-terminated oligoamide intermediate, in another embodiment no more than about 2.5 moles of monoalcohol per every 1 mole of acid-terminated oligoamide intermediate, and in yet another embodiment no more than about 2.4 moles of monoalcohol per every 1 mole of acid-terminated oligoamide intermediate, although the relative amounts can be outside of these ranges.

The acid-terminated oligoamide and the coupling agent are present in any desired or effective relative amounts, in one embodiment at least about 1.8 moles of coupling agent per every 1 mole of diacid diamide, in another embodiment at least about 2 moles of coupling agent per every 1 mole of diacid diamide, and in yet another embodiment at least about 2.2 moles of coupling agent per every one mole of diacid diamide, and in one embodiment no more than about 3 moles of coupling agent per every 1 mole of diacid diamide, in another embodiment no more than about 2.8 moles of coupling agent per every 1 mole of diacid diamide, and in yet another embodiment no more than about 2.5 moles of coupling agent per every 1 mole of diacid diamide, although the relative amounts can be outside of these ranges.

The catalyst and the acid-terminated oligoamide intermediate are present in any desired or effective relative amounts, in one embodiment at least about 0.05 mole of catalyst per every 1 mole of acid-terminated oligoamide intermediate, in another embodiment at least about 0.1 moles of catalyst per every 1 mole of acid-terminated oligoamide intermediate, and in yet another embodiment at least about 0.2 mole of catalyst per every one mole of acid-terminated oligoamide intermediate, and in one embodiment no more than about 1 mole of catalyst per every 1 mole of acid-terminated oligoamide intermediate, in another embodiment no more than about 0.8 mole of catalyst per every 1 mole of acid-terminated oligoamide intermediate, and in yet another embodiment no more than about 0.5 mole of catalyst per every 1 mole of acid-terminated oligoamide intermediate, although the relative amounts can be outside of these ranges.

Any desired or effective solvent can be employed. Examples of suitable solvents include methylene chloride, tetrahydrofuran, methyl ethyl ketone, toluene, dimethyl formamide, diethyl ether, hexane, ethyl acetate, and the like, as well as mixtures thereof.

The solvent can be present in any desired or effective amount, in one embodiment at least about 20 milliliters of solvent per gram of acid-terminated oligoamide intermediate, in another embodiment at least about 25 milliliters of solvent per gram of acid-terminated oligoamide intermediate, and in yet another embodiment at least about 30 milliliters of solvent per gram of acid-terminated oligoamide intermediate, and in one embodiment no more than about 100 milliliters of solvent per gram of acid-terminated oligoamide intermediate, in another embodiment no more than about 90 milliliters of solvent per gram of acid-terminated oligoamide intermediate, and in yet another embodiment no more than about 80 milliliters of solvent per gram of acid-terminated oligoamide intermediate, although the amount of solvent can be outside of these ranges.

The reaction between the acid-terminated oligoamide intermediate, the monoalcohol, and the coupling agent can be carried out at any desired or effective temperature, in one embodiment at least about 15° C., in another embodiment at least about 20° C., and in yet another embodiment at least about 25° C., and one embodiment no more than about 40° C., in another embodiment no more than about 35° C., and in yet another embodiment no more than about 30° C., although the temperature can be outside of these ranges.

The reaction between the acid-terminated oligoamide intermediate, the monoalcohol, and the coupling agent can be carried out for any desired or effective period of time, in one embodiment at least about 2 hours, in another embodiment at least about 2.5 hours, and in yet another embodiment at least about 3 hours, and in one embodiment no more than about 5 hours, in another embodiment no more than about 4.5 hours, and in another embodiment no more than about 4 hours, although the period of time can be outside of these ranges.

Subsequent to completion of the reaction, the product can be recovered by any desired or effective method, such as filtration of any solid by-products or washing the solution with water depending on the coupling agent used. The solvent can be removed by rotary evaporation. If needed, the product can be purified by washing with acetone and dried in a vacuum oven.

Analogous procedures can be employed using amine compounds of the formula $HNR_3R_4$ in place of monoalcohols of the formula $R_3OH$.

Many embodiments of the compounds thus prepared can exhibit gel-like behavior in that they undergo a relatively sharp increase in viscosity over a relatively narrow temperature range when dissolved in a liquid such as those compounds that behave as curable monomers when exposed to radiation such as ultraviolet light. One example of such a material is a propoxylated neopentyl glycol diacrylate such as SR9003, commercially available from Sartomer Co. Inc. In one embodiment, some compounds as disclosed herein undergo a change in viscosity of at least about $10^3$ centipoise, in another embodiment at least about $10^5$ centipoise, and in yet another embodiment at least about $10^6$ centipoise over a temperature range of in one embodiment at least about 30° C., in another embodiment at least about 10° C., and in yet another embodiment at least about 5° C., although the viscosity change and temperature range can be outside of these ranges, and compounds that do not undergo changes within these ranges are also included herein.

At least some embodiments of the compounds disclosed herein can form a semi-solid gel at a first temperature. For example, when the compound is incorporated into a phase change ink, this temperature is below the specific temperature at which the ink is jetted. The semi-solid gel phase is a physical gel that exists as a dynamic equilibrium comprising one or more solid gellant molecules and a liquid solvent. The semi-solid gel phase is a dynamic networked assembly of molecular components held together by non-covalent interactions such as hydrogen bonding, Van der Waals interactions, aromatic non-bonding interactions, ionic or coordination bonding, London dispersion forces, or the like, which, upon stimulation by physical forces, such as temperature, mechanical agitation, or the like, or chemical forces, such as pH, ionic strength, or the like, can undergo reversible transitions from liquid to semi-solid state at the macroscopic level. The solutions containing the gellant molecules exhibit a thermally reversible transition between the semi-solid gel state and the liquid state when the temperature is varied above or below the gel point of the solution. This reversible cycle of transitioning between semi-solid gel phase and liquid phase can be repeated many times in the solution formulation.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

PRIPOL® 1009 dimer diacid (2 eq, 10 mmoles, 5.78 g; obtained from Uniqema, New Castle, Del.) was dissolved in 75 mL dichloromethane in a 250 mL round bottomed flask under inert atmosphere. The solution was then cooled to 0° C. and 4-dimethylaminopyridine (DMAP; 0.2 eq, 2 mmoles, 0.24 g; obtained from Sigma-Aldrich Fine Chemicals, Milwaukee, Wis.) was added. After the DMAP was completely dissolved, a solution of 1,3-dicyclohexylcarbodiimide (DCC; 1 M in dichloromethane, 4 eq, 20 mmoles, 20 mL; obtained from Sigma-Aldrich Fine Chemicals) was added. After the solution was stirred for 30 minutes, ethylene diamine (1 eq, 5 mmoles, 0.3 g; obtained from Sigma-Aldrich Fine Chemicals) was added and stirred for 2 hours at room temperature. Thereafter, a solution of 1-(4-(2-hydroxyethoxy)phenyl)-2-hydroxy-2-methylpropan-1-one (IRGACURES® 2959, obtained from Ciba Specialty Chemicals, Basel, Switzerland, 2 eq, 10 mmoles, 2.24 g) in 20 mL of dichloromethane was added, and the solution was brought to room temperature and stirred for 2 hours. The reaction mixture was then filtered to remove N,N'-dicyclohexylurea byproduct (DCHU). The solvents were subsequently removed from the filtrate by rotary evaporation. The crude product was washed with acetone, filtered, and dried in a vacuum oven. The di-photoinitiator capped gellant was obtained as a white semi-solid in 67.76% yield (5.43 g). The product was believed to be of the following formula:

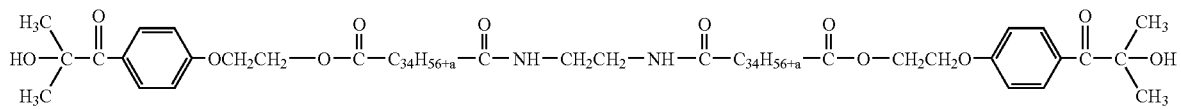

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

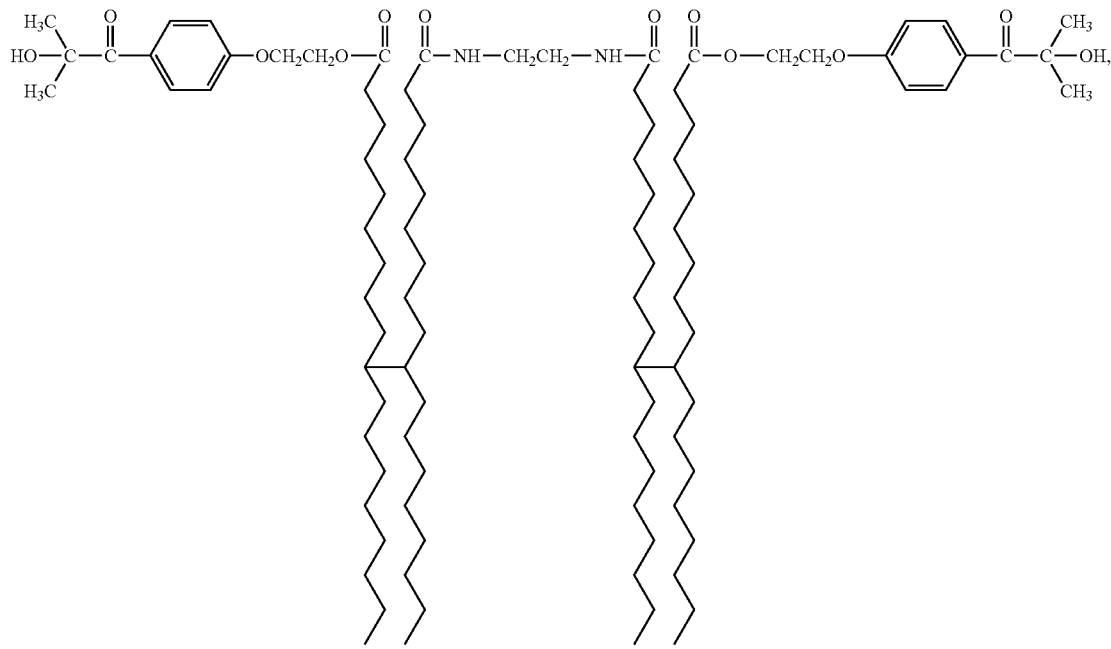

EXAMPLE II

PRIPOL® 1009 dimer diacid (2 eq, 10 mmoles, 5.78 g; obtained from Uniqema, New Castle, Del.) was dissolved in 75 mL dichloromethane in a 250 mL round bottomed flask under inert atmosphere. The solution was then cooled to 0° C. and 4-dimethylaminopyridine (DMAP; 0.2 eq, 2 mmoles, 0.24 g; obtained from Sigma-Aldrich Fine Chemicals, Milwaukee, Wis.) was added. After the DMAP was completely dissolved, a solution of 1,3-dicyclohexylcarbodiimide (DCC; 1 M in dichloromethane, 4 eq, 20 mmoles, 20 mL; obtained from Sigma-Aldrich Fine Chemicals) was added. After the solution was stirred for 30 minutes, ethylene diamine (1 eq, 5 mmoles, 0.3 g; obtained from Sigma-Aldrich Fine Chemicals) was added and stirred for 2 hours at room temperature. Thereafter, caprolactone acrylate (TONE® M100, obtained from Dow Chemical Co., Midland, Mich.; 1 eq, 5 mmoles, 1.72 g) and a 20 mL solution of 1-(4-(2-hydroxyethoxy)phenyl)-2-hydroxy-2-methylpropan-1-one (IRGACURE® 2959; 1 eq, 5 mmoles, 1.12 g, obtained from Ciba Specialty Chemicals, Basel, Switzerland) in dichloromethane was added and stirred 2 hours at ambient temperature. The reaction mixture was filtered to remove N,N'-dicyclohexylurea byproduct (DCHU). The solvents were subsequently removed from the filtrate by rotary evaporation. The crude product was washed with acetone, filtered, and dried in vacuum oven. The product was believed to be a mixture of the following compounds:

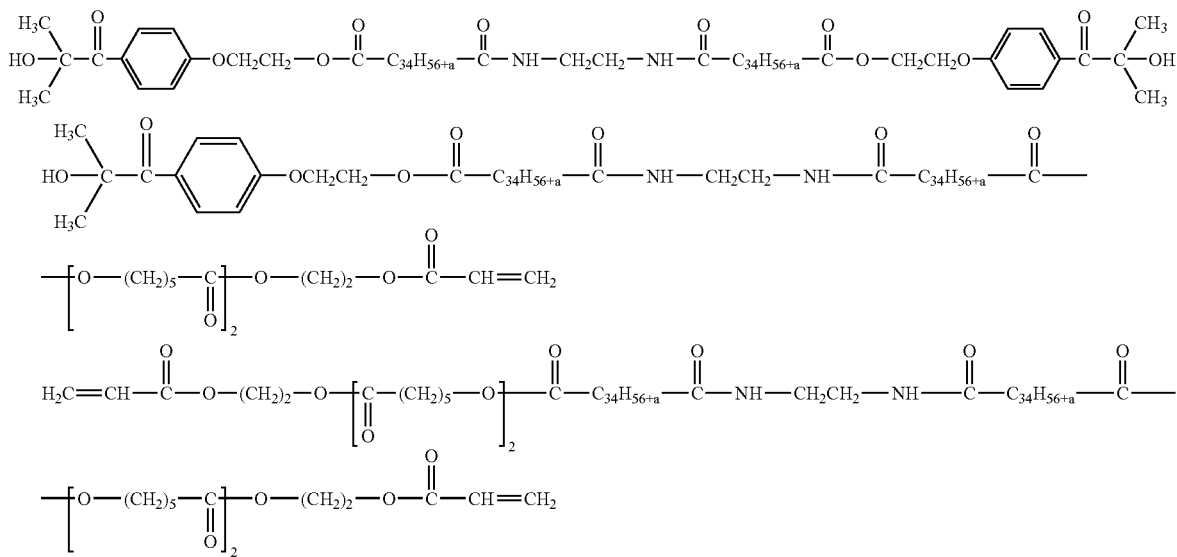

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

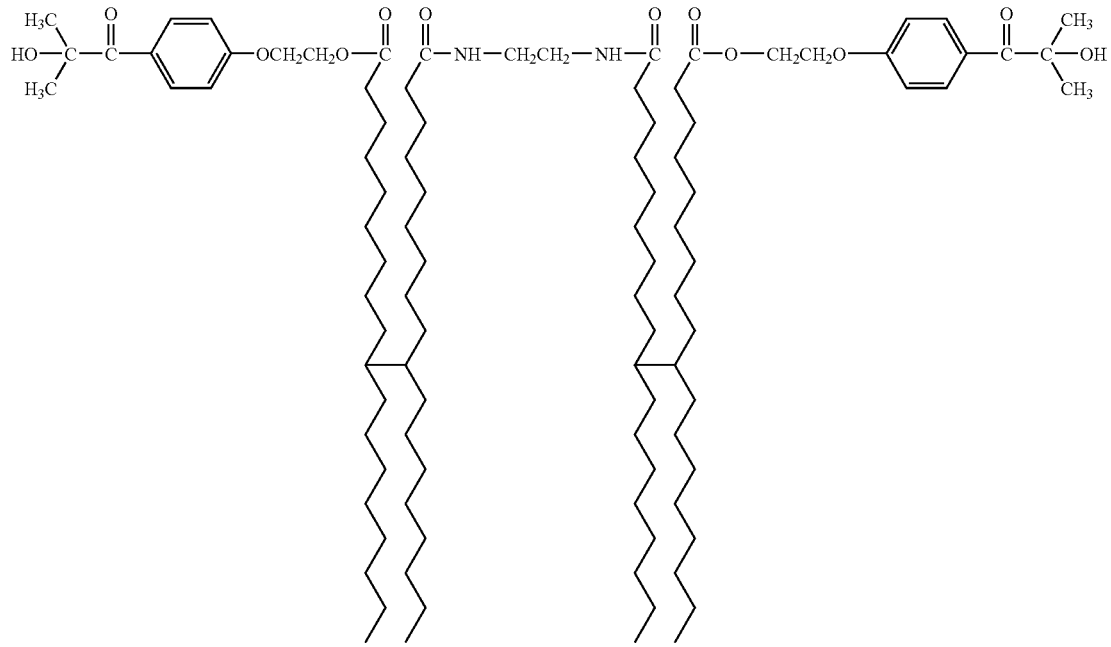

-continued
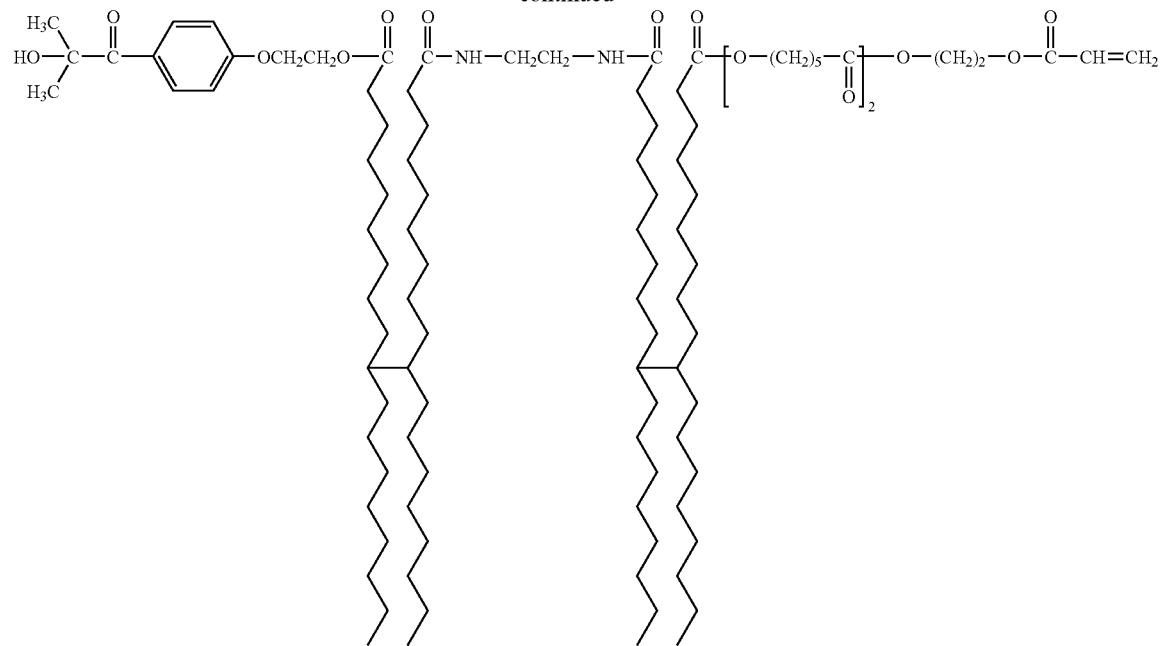
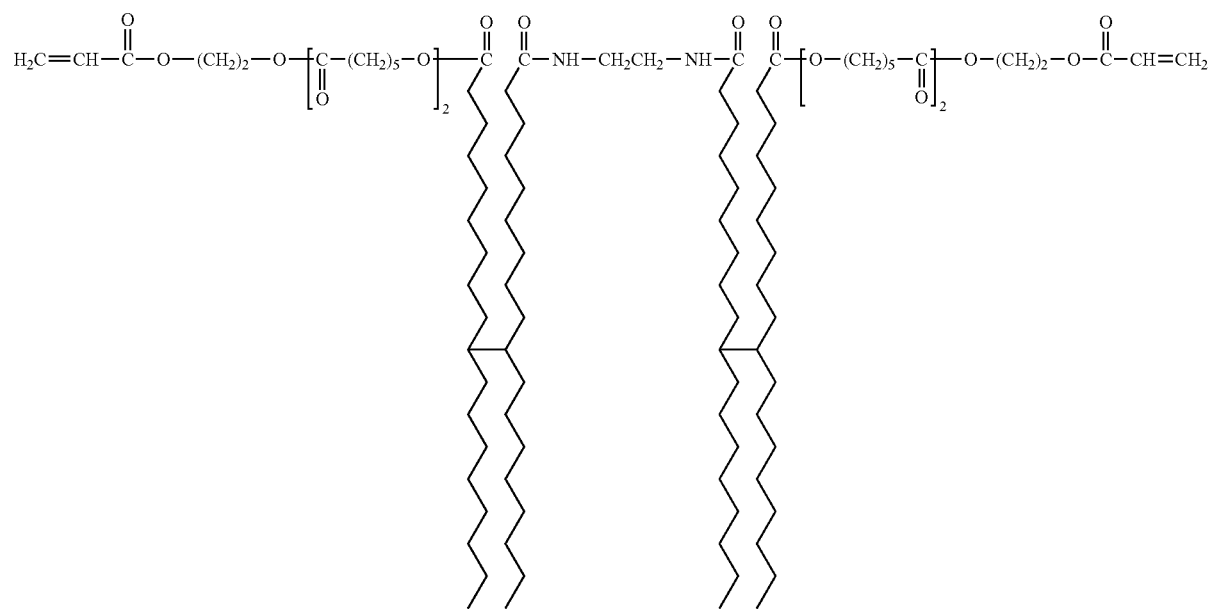
EXAMPLE III
Compounds of the formula

wherein —$C_{34}H_{56+a}$— resents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

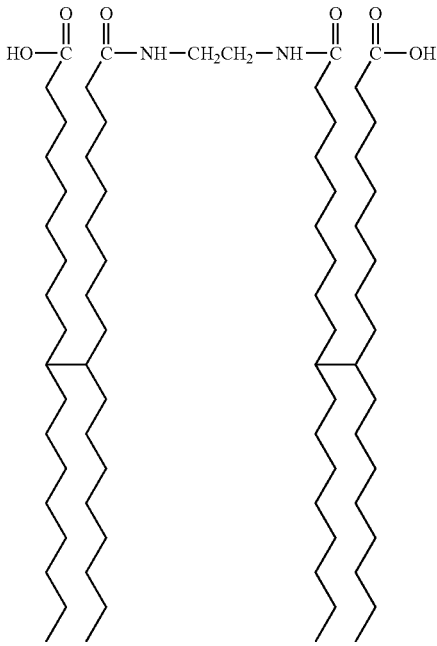

were prepared as follows. To a 4 neck, 1 L reaction kettle equipped with a thermocouple, overhead stirrer, stopper, Dean-Stark trap, reflux condenser, and argon inlet was added PRIPOL® 1009 (C36 dimer acid mixture, including isomers of the formula

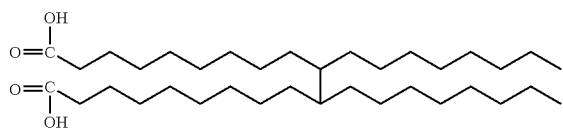

as well as other branched isomers which may include unsaturations and cyclic groups; 850 g, acid number 196 mgKOH/g, 95 wt %, obtained from Uniqema, New Castle, Del.; further information on C36 dimer acids of this type is disclosed in, for example, "Dimer Acids," Kirk-Othmer Encyclopedia of Chemical Technology, Vol. 8, 4$^{th}$ Ed. (1992), pp. 223 to 237, the disclosure of which is totally incorporated herein by reference) and IRGAFOS® 168 (tris(2,4-di-(tert)-butylphenyl) phosphate, 1.79 g, 0.2 wt %, obtained from Ciba Specialty Chemicals, Basel, Switzerland). The system was purged with Ar for 15 minutes with one of the necks open, after which time the stopper was replaced. The temperature was set to 100° C. and the stirrer was set in motion. The stopper was quickly replaced with an addition funnel equipped with a septum, and ethylene diamine (EDA, 44.6 g, 49.6 mL, 5 wt %, obtained from Sigma-Aldrich Chemical Company, Milwaukee, Wis.) was added via syringe. The EDA was added to the reaction mixture slowly dropwise, ensuring that the internal reaction temperature did not exceed 118° C. After the addition was complete, the temperature was raised slowly stepwise to 155° C., where it was kept until water ceased collecting in the Dean-Stark trap (about 14 mL $H_2O$ collected; reaction time was 2-3 h at 155° C.). The completion of the reaction was confirmed by $^1$H NMR analysis in $CDCl_3$: the triplet at δ2.34, corresponding to the protons alpha to the carboxylic acid groups, and the triplet at δ2.18, corresponding to the protons alpha to the carbonyl groups of the amides, were in approximately a 1:1 ratio. At the end of the reaction, the temperature was lowered to 130° C. and the clear, amber oil was poured from the reaction kettle into aluminum plates (recovered m=867 g). Acid number=94.8 mgKOH/g. $^1$H NMR ($CDCl_3$, 300 MHz) δ3.38 (4H, br. s), 2.53 (2H, br. s), 2.34 (4H, t, J=7.3 Hz), 2.18 (4H, t, J=7.6 Hz), 1.88-0.65 (136H, m).

EXAMPLE IV

Compounds of the formula

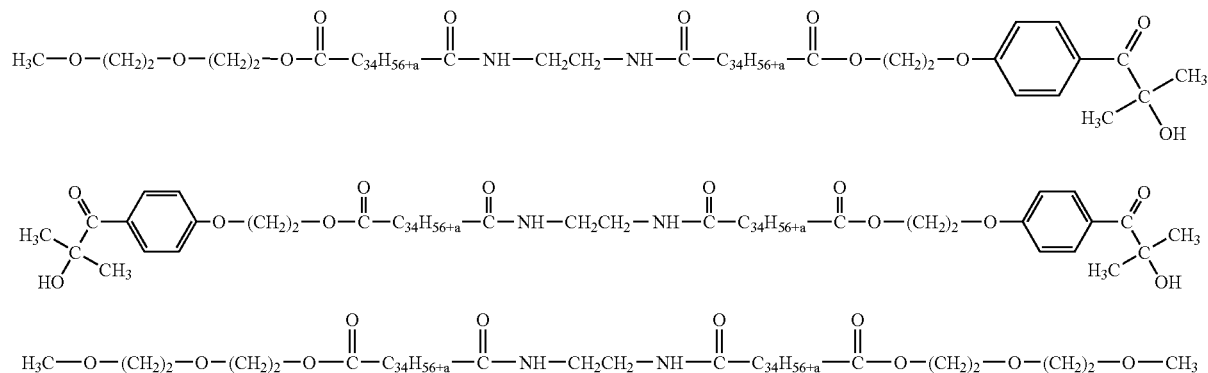

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

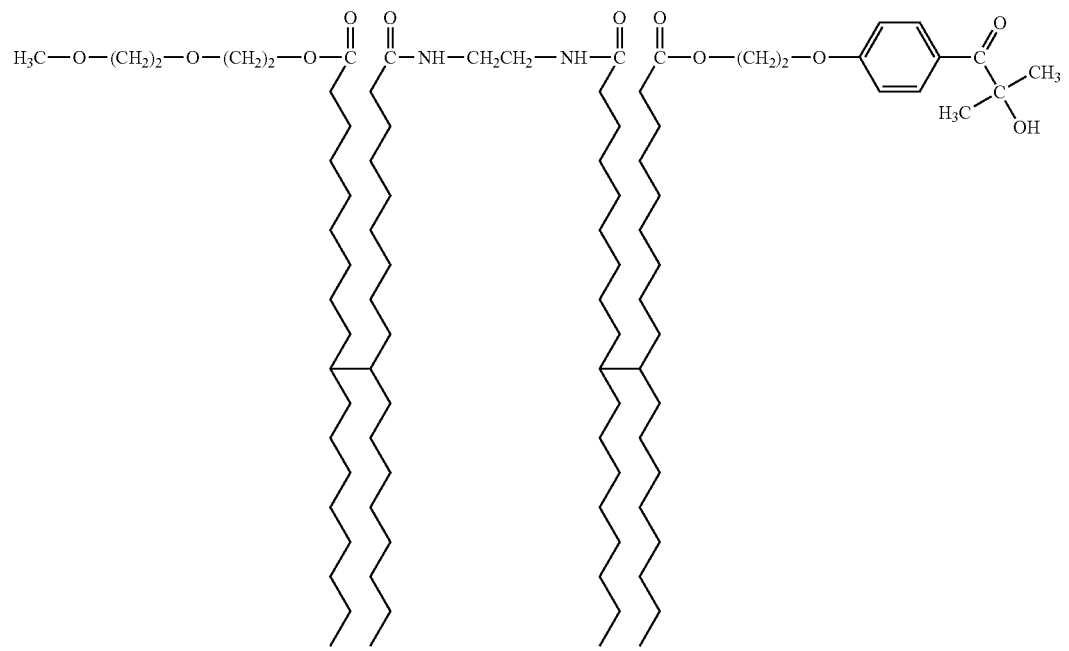
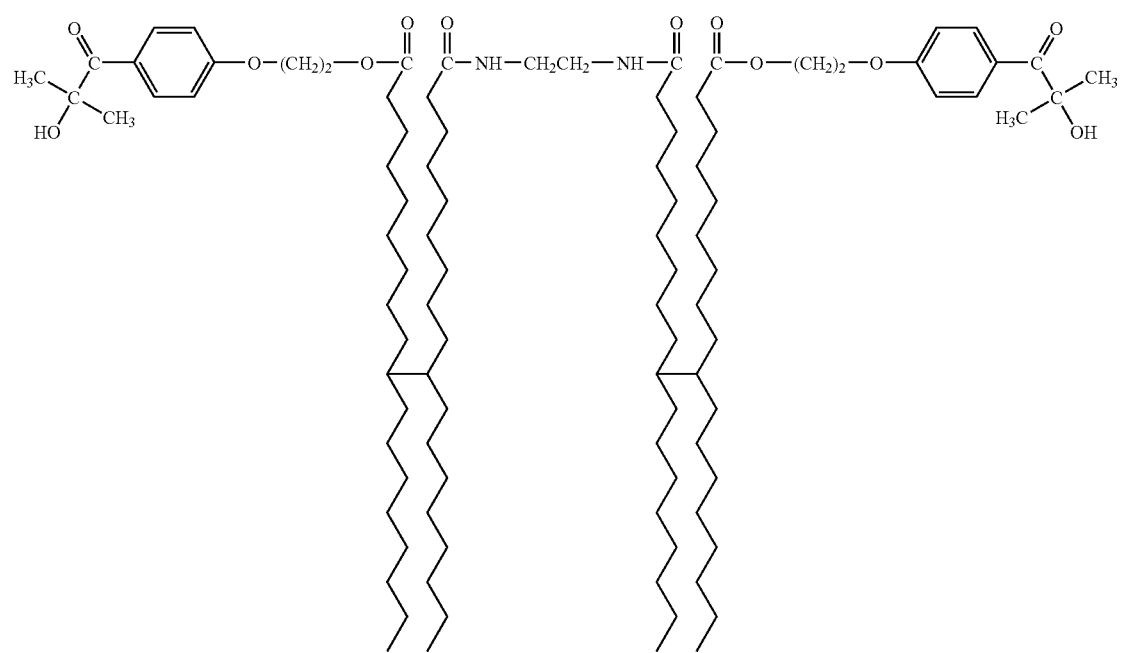

-continued

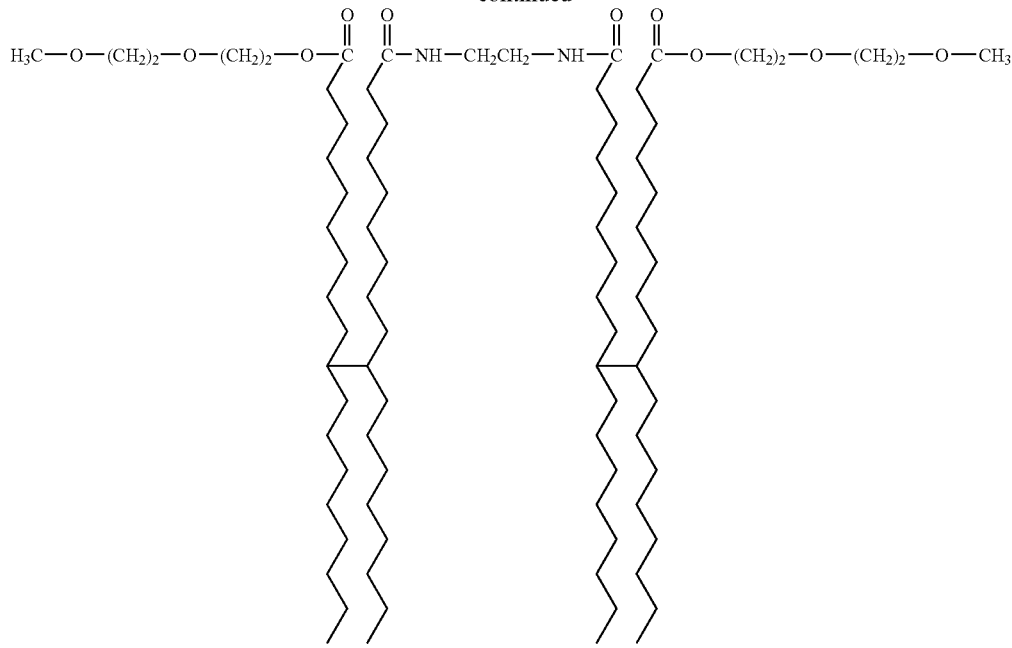

were prepared as follows. To a 3 neck, 2 L flask equipped with two dropping funnels, stir bar and argon inlet was added the organoamide prepared in Example III (50 g, acid number 94.8, $n_{acid}=8.45\times10^{-2}$ mol), 4-dimethylaminopyridine (1.03 g, $8.45\times10^{-3}$ mol, obtained from Sigma-Aldrich Chemical Company, Milwaukee, Wis.), and methylene chloride (850 mL) and the reaction mixture was stirred until homogenous. 1,3-Dicyclohexylcarbodiimide (101 mL, 1 M solution in $CH_2Cl_2$, $1.01\times10^{-1}$ mol, obtained from Sigma-Aldrich Chemical Company, Milwaukee, Wis.) was added slowly dropwise and the reaction mixture was allowed to stir for 0.5 h before adding diethylene glycol methyl ether (5.08 g, $4.23\times10^{-2}$ mol, obtained from Sigma-Aldrich Chemical Company, Milwaukee, Wis.) slowly dropwise concurrently with 1-(4-(2-hydroxyethoxy)phenyl)-2-hydroxy-2-methyl-propan-1-one (IRGACURE® 2959; 9.47 g, $4.22\times10^{-2}$ mol; obtained from Ciba Specialty Chemicals, Basel, Switzerland) portionwise. The reaction progress was followed via $^1H$ NMR spectroscopy in $CDCl_3$: when the signals corresponding to the methylene protons from both alcohols (m, ca. δ3.74 from diethylene glycol methyl ether and m, ca. δ4.03 from 1-(4-(2-hydroxyethoxy)phenyl)-2-hydroxy-2-methylpropan-1-one) were consumed, the reaction was complete. The reaction time was typically between 2-3 h. The reaction mixture was filtered to remove N,N'-dicyclohexylurea (byproduct) and the filtrate solvent was removed in vacuo, Methanol (250 mL) was added to the residue and a biphasic mixture formed that was transferred to a separatory funnel. The bottom layer was removed, dissolved in $CH_2Cl_2$ (250 mL), dried over $MgSO_4$ and filtered. The solvent was removed in vacuo to reveal a pale yellow foam (54.5 g). $^1H$ NMR ($CDCl_3$, 300 MHz) δ8.08 (2H, d, J=8.9 Hz), 6.97 (2H, d, J=8.9 Hz), 4.47-4.44 (2H, m), 4.26-4.22 (4H, m), 3.72-3.54 (6H, m), 3.40-3.30 (7H, m), 2.71-2.45 (3H, br. s), 2.38-2.30 (4H, m), 2.17 (4H, t, J=7.5 Hz), 1.90-0.60 (132H, m).

EXAMPLE V

The process of Example IV was repeated replacing the diethylene glycol methyl ether with di(propylene glycol) methyl ether (mixture of isomers, 6.26 g, $4.22\times10^{-2}$ mol, obtained from Sigma-Aldrich Chemical Company, Milwaukee, Wis.). The product was a pale yellow foam (55.0 g). $^1H$ NMR ($CDCl_3$, 300 MHz) δ8.08 (2H, $d_1$, $J_{d1}$=9.0 Hz and $d_2$, $J_{d2}$=9.0 Hz), 6.97 (2H, $d_1$, $J_{d1}$=9.0 Hz and $d_2$, $J_{d2}$=9.0 Hz), 5.18-4.99 (0.5H, m), 4.47-4.44 (2H, m), 4.26-4.23 (2H, m), 4.05 (0.2H, d, J=5.3 Hz), 3.64-3.26 (12H, m), 2.65-2.45 (3H, br. s), 2.41-2.26 (4H, m), 2.17 (4H, t, J=7.6 Hz), 1.93-0.83 (138H, m). It is believed that the products were of the formulae

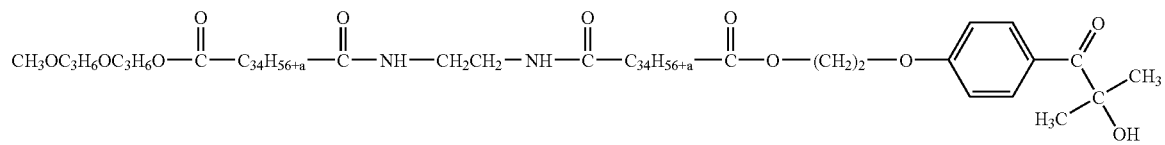

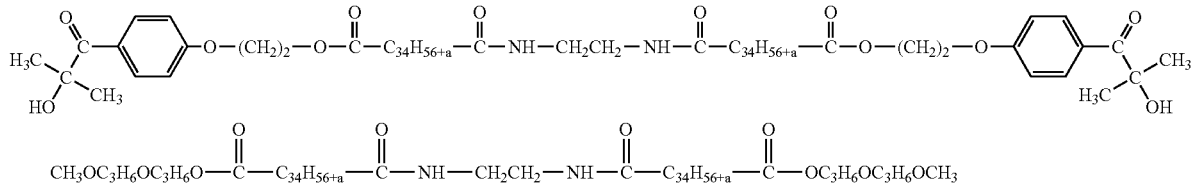
wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula
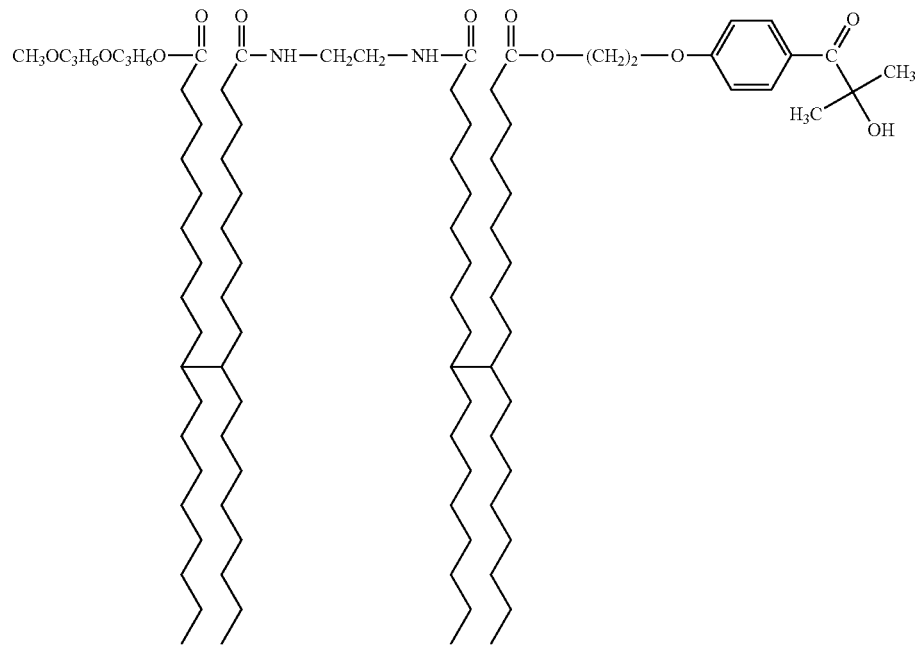
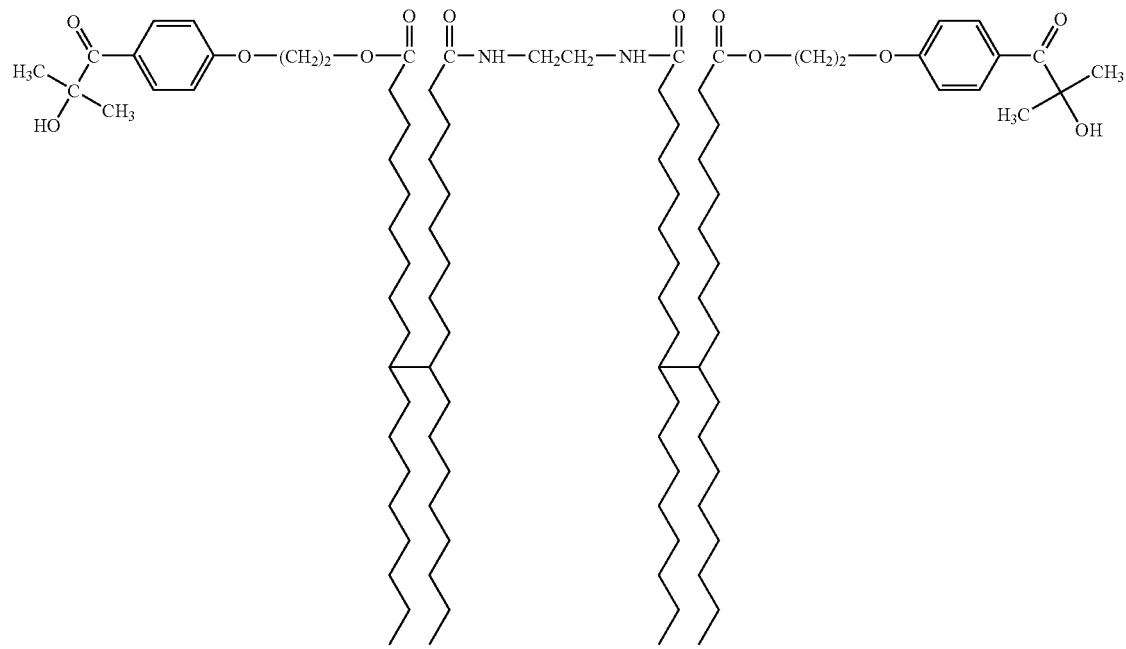

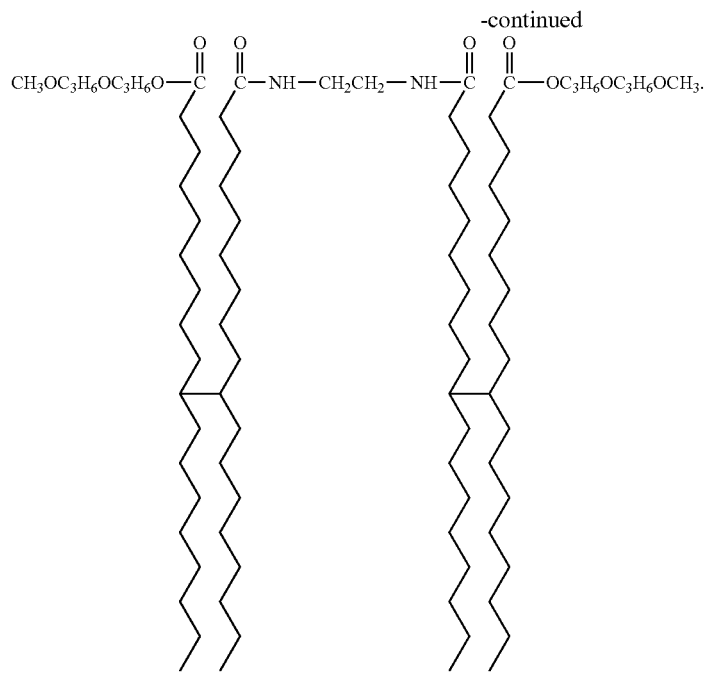

EXAMPLE VI

The process of Example IV was repeated replacing the diethylene glycol methyl ether with triethylene glycol monomethyl ether (6.94 g, 4.23×10$^{-2}$ mol, obtained from Sigma-Aldrich Chemical Company, Milwaukee, Wis.). The product was a pale yellow foam (50.0 g). $^1$H NMR (CDCl$_3$, 300 MHz) δ8.08 (2H, d, J=8.7 Hz), 6.97 (2H, d, J=8.7 Hz), 4.54-4.33 (2H, m), 4.26-4.21 (4H, m), 3.71-3.54 (10H, m), 3.46-3.29 (7H, m), 2.65-2.44 (3H, br. s), 2.44-2.25 (4H, m), 2.19 (4H, t, J=7.4 Hz), 2.03-0.62 (142H, m). It is believed that the products were of the formula

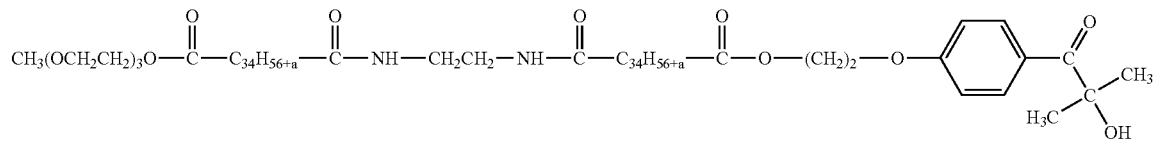

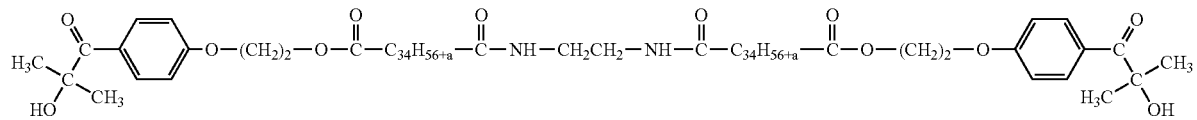

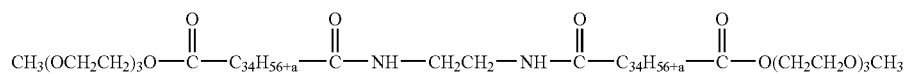

wherein —C$_{34}$H$_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

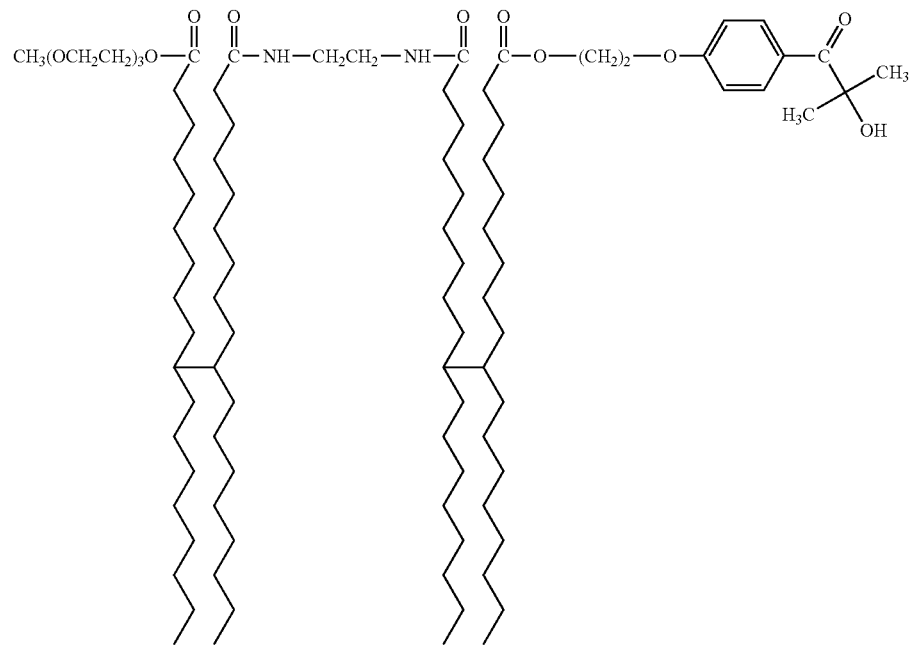
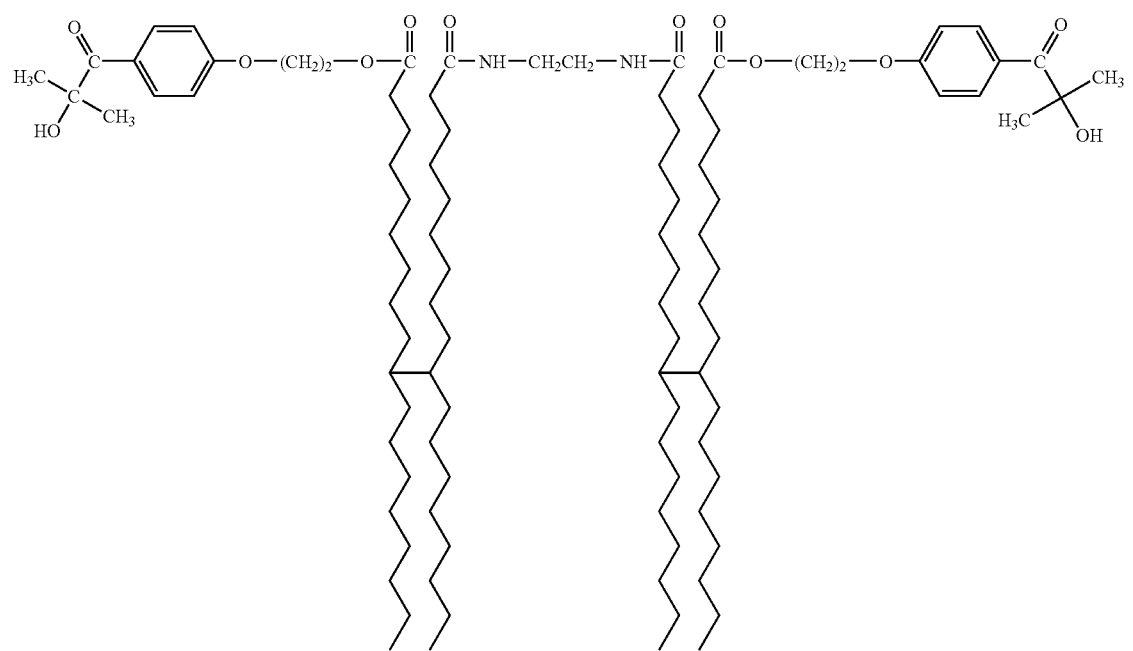

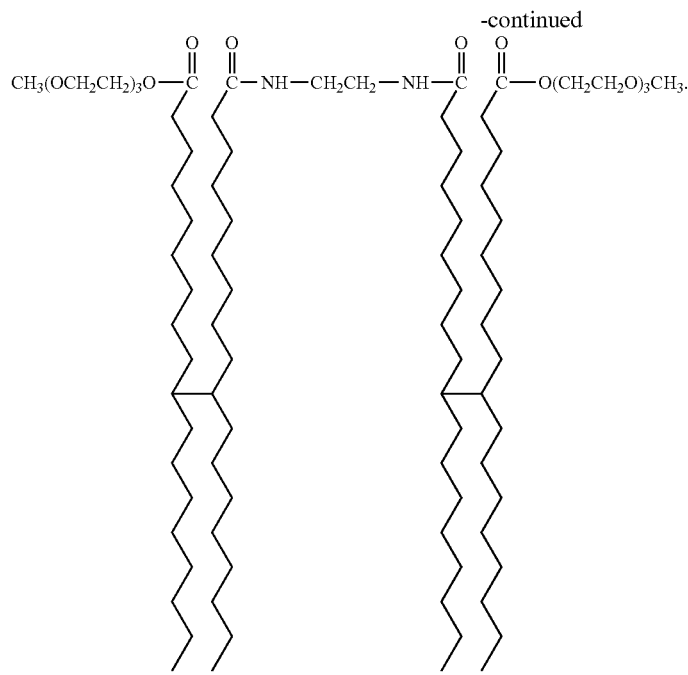

EXAMPLE VII

The process of Example IV was repeated replacing the ene glycol methyl ether with tri(propylene glycol)methyl ether (mixture of isomers, 8.71 g, $4.22 \times 10^{-2}$ mol, obtained from Sigma-Aldrich Chemical Company, Milwaukee, Wis.). The product was a pale yellow foam (53.1 g). $^1$H NMR (CDCl$_3$, 300 MHz) $\delta$8.08 (2H, d$_1$, J$_{d1}$=8.6 Hz and d$_2$, J$_{d2}$=8.7 Hz), 6.97 (2H, d$_1$, J$_{d1}$=8.6 Hz and d$_2$, J$_{d2}$=8.7 Hz), 5.15-4.92 (0.4H, m), 4.56-4.37 (2H, m), 4.30-4.13 (2.2H, m), 3.82-3.23 (15H, m), 2.65-2.47 (3H, br. s), 2.47-2.24 (4H, m), 2.17 (4H, t, J=7.5 Hz), 2.04-0.47 (162H, m). It is believed that the products were of the formula

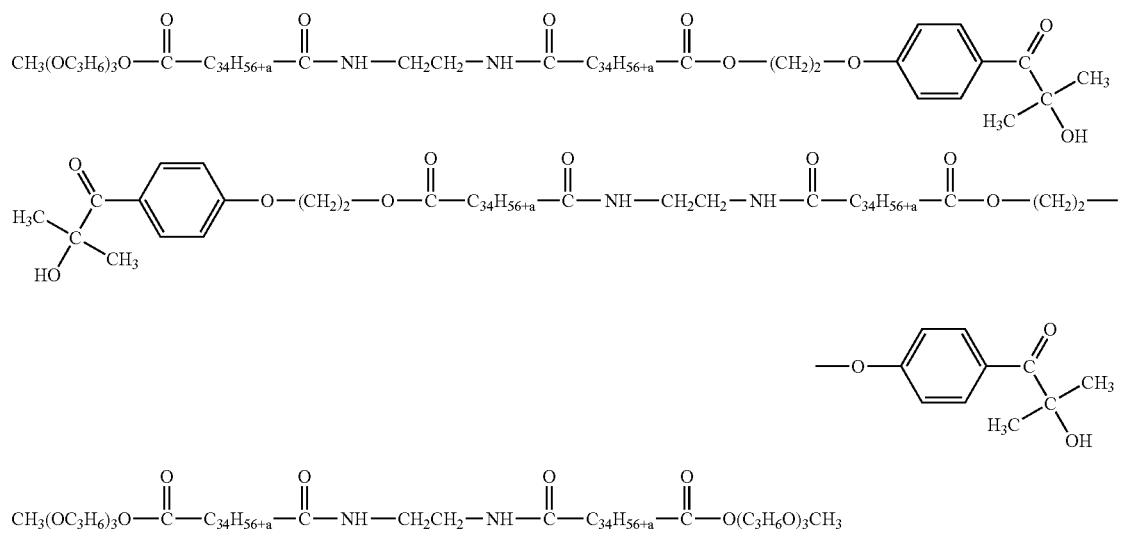

wherein —C$_{34}$H$_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

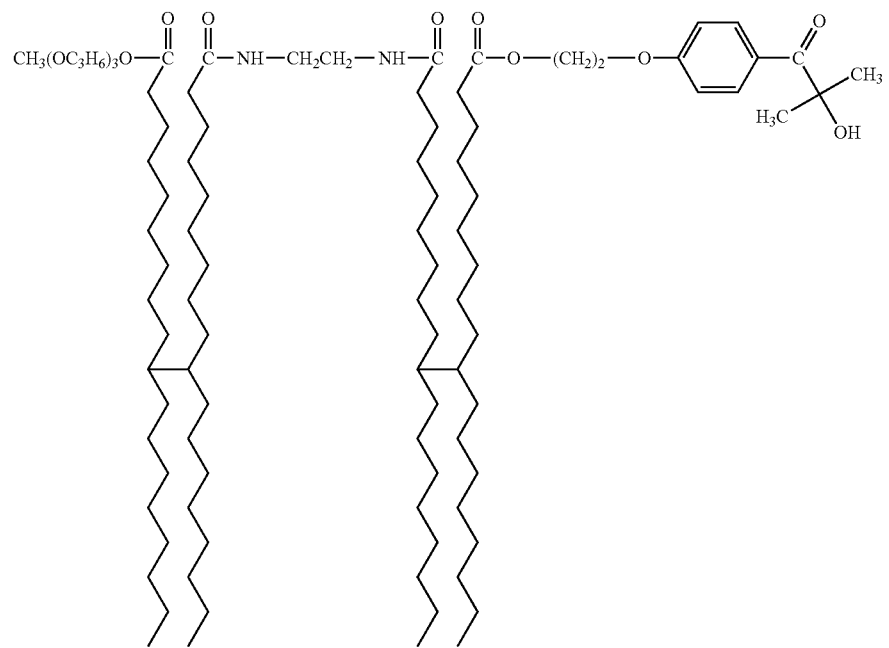
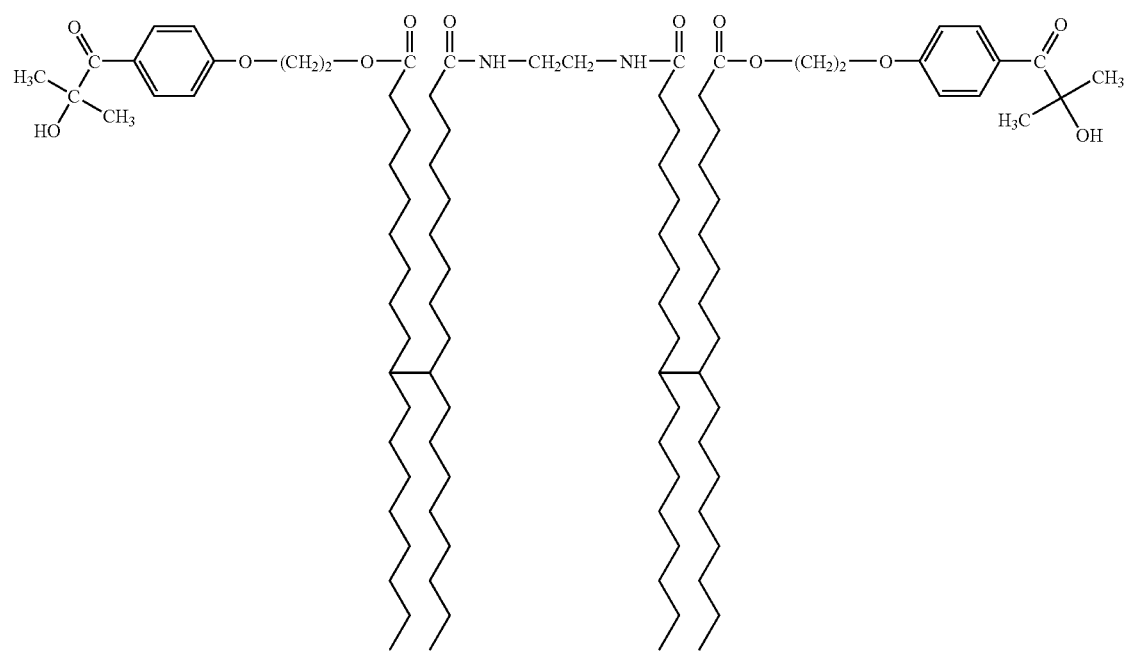

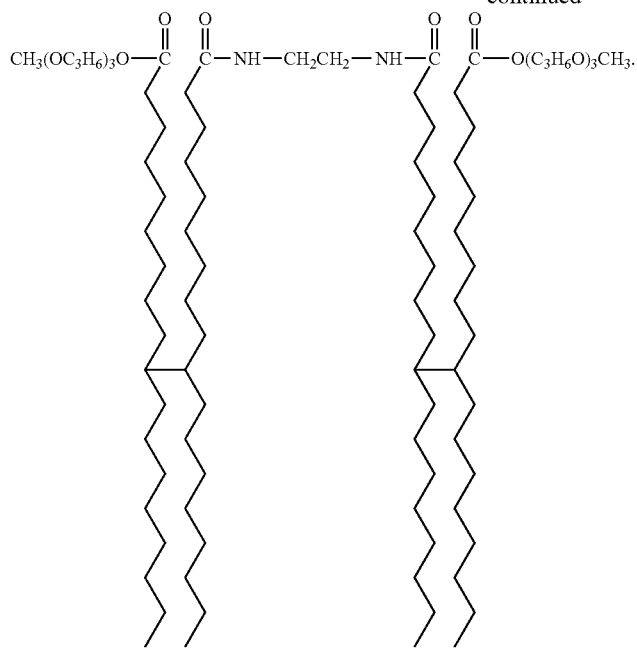

EXAMPLE VIII

The process of Example IV was repeated replacing the diethylene glycol methyl ether with caprolactone acrylate (TONE® M100, 14.52 g, 4.22×10$^{-2}$ mol, obtained from Dow Chemical Co., Midland, Mich.). The product was a sticky, pale yellow solid (47.1 g). $^1$H NMR (CDCl$_3$, 300 MHz) δ8.08 (2H, d, J=8.7 Hz), 6.97 (2H, d, J=8.7 Hz), 6.47 (1H, d, J=17.4 Hz), 6.15 (1H, dd, J=17.4, 10.4 Hz), 5.89 (1H, d, J=10.4 Hz), 4.47 (2H, t, J=4.6 Hz), 4.40-4.23 (6H, m), 4.08 (4H, t, J=6.6 Hz), 3.37 (4H, s), 2.69-2.45 (3H, br. s), 2.45-2.26 (8H, m), 2.19 (4H, t, J=7.3 Hz), 1.99-0.83 (160H, m). It is believed that the products were of the formula

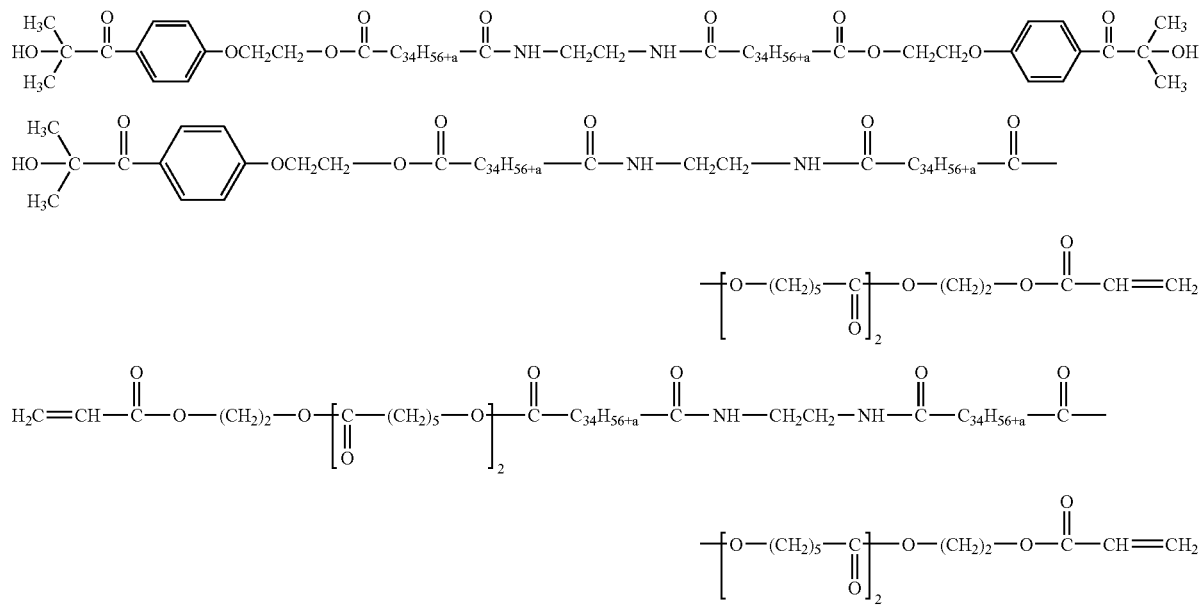

wherein —C$_{34}$H$_{56+a}$— represents a branched alkylene group which may include unsaturations and cyclic groups, wherein a is an integer of 0, 1, 2, 3, 4, 5, 6, 7, 8, 9, 10, 11, or 12, including (but not limited to) isomers of the formula

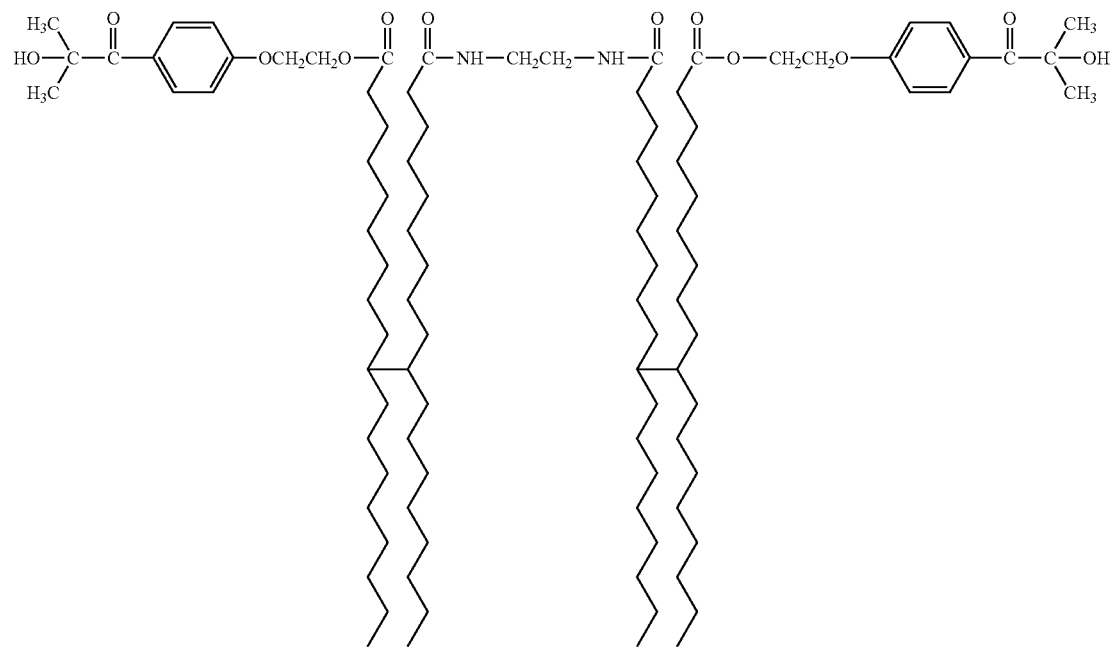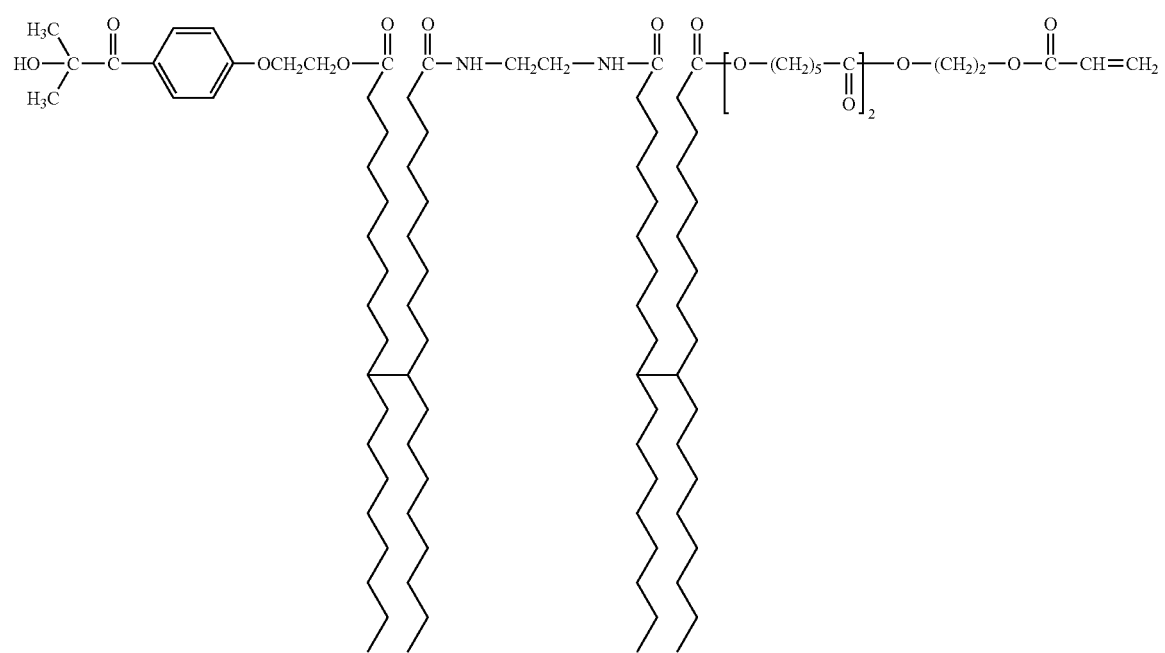

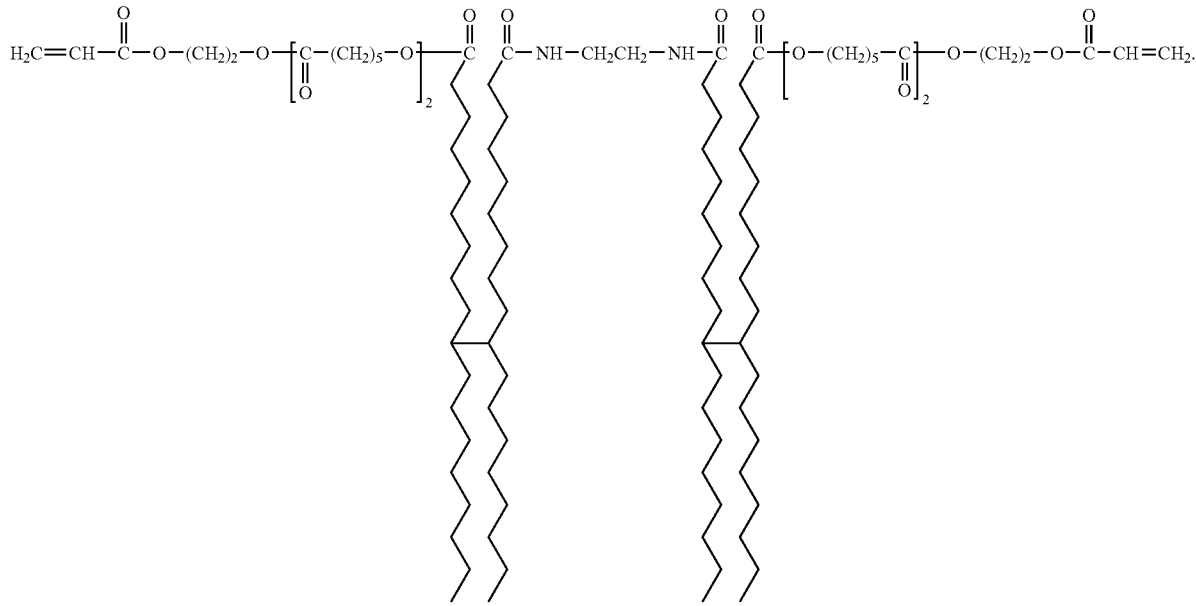

EXAMPLE IX

The process of Example I is repeated replacing the 1-(4-(2-hydoxyethoxy)phenyl)-2-hydroxy-2-methylpropan-1-one (IRGACURE® 2959) with N,N-dimethylethanolamine (2 eq, 10 mmoles, 0.89 g; commercially available from Sigma-Aldrich Fine Chemicals, Milwaukee, Wis.). It is believed that the product will be of the formula

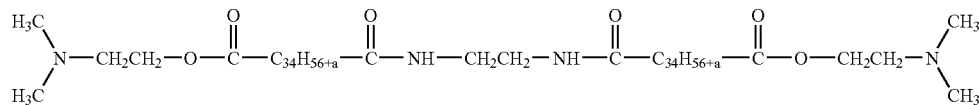

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11, or 12 including (but not limited to) isomers of the formula

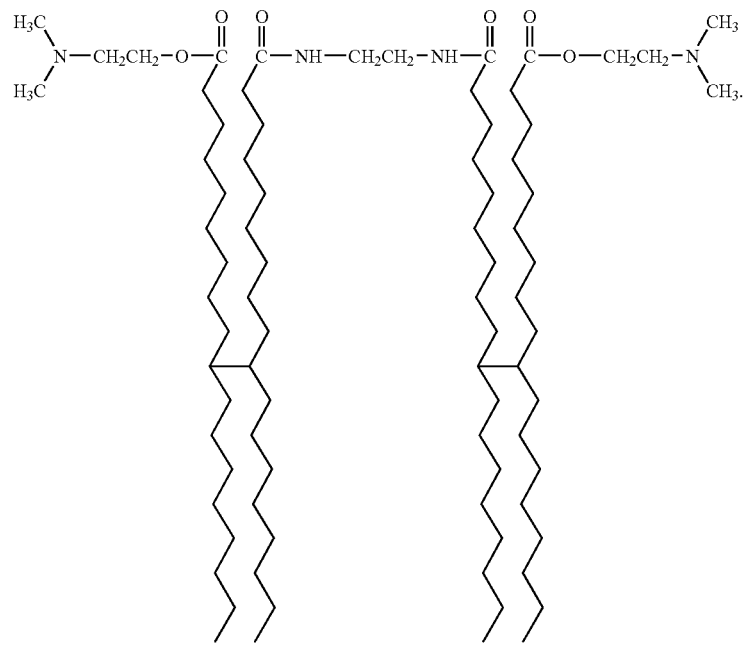

EXAMPLE X

The process of Example I is repeated replacing the 1-(4-(2-hydroxyethoxy)phenyl)-2-hydroxy-2-methylpropan-1-one (IRGACURE® 2959) with N,N-dimethylethylenediamine (2 eq, 10 mmoles, 0.88 g; commercially available from Sigma-Aldrich Fine Chemicals, Milwaukee, Wis.). It is believed that the product will be of the formula

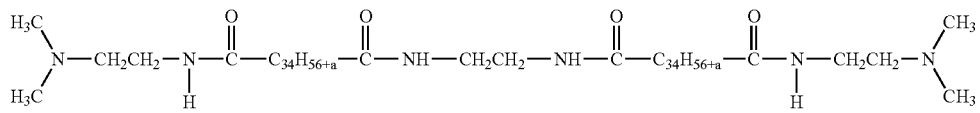

wherein —$C_{34}H_{56+a}$— represents a branched alkylene group which may include unsaturations and cyclic groups, wherein a is an integer of 0, 1, 2, 3, 4, 5, 6, 7, 8, 9, 10, 11 or 12 including (but not limited to) isomers of the formula

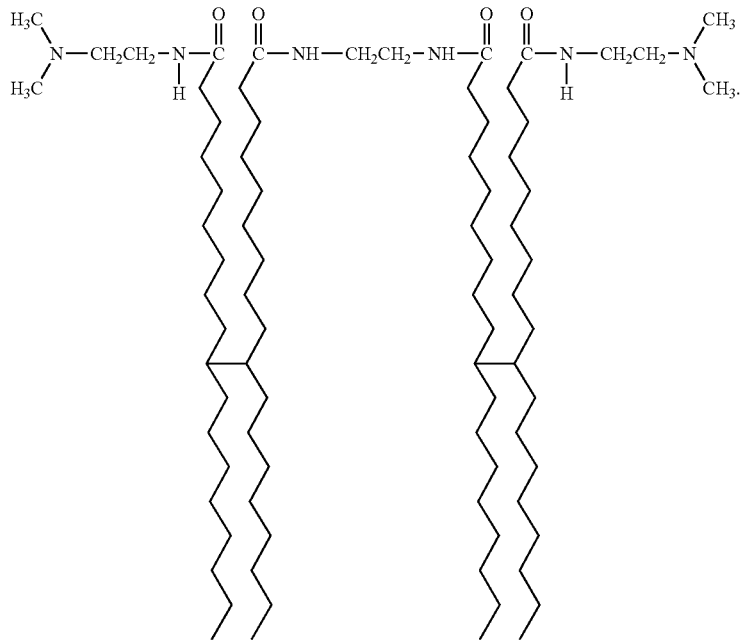

INK EXAMPLES A THROUGH E

The desired amide gellant, propoxylated neopentyl glycol diacrylate (SR9003, obtained from Sartomer Co. Inc., Exton, Pa.), 2-dimethylamino-2-(4-methylbenzyl)-1-(4-morpholin-4-ylphenyl)-butanone (IRGACURE® 379, obtained from Ciba Specialty Chemicals, Tarrytown, N.Y.), isopropyl-9H-thioxanthen-9-one (DAROCUR® ITX, obtained from Ciba Specialty Chemicals, Tarrytown, N.Y.), bis(2,4,6-trimethylbenzoyl)-phenyl-phosphine oxide (IRGACURE® 819, obtained from Ciba Specialty Chemicals, Tarrytown, N.Y.), 2-hydroxy-1-(4-(4-(2-hydroxy-2-methyl-propionyl)-benzyl)-phenyl)-2-methylpropan-1-one (IRGACURE® 127, obtained from Ciba Specialty Chemicals, Tarrytown, N.Y.), and IRGASTAB® UV10 (obtained from Ciba Specialty Chemicals, Tarrytown, N.Y.) were admixed and stirred for 1 h at 90° C. The resulting solution was added dropwise to a stirring solution of SUN BLUE pigment dispersion, 25 wt % (obtained from Sun Chemical, Parsippany, N.J.), also at 90° C. The ink thus prepared was allowed to stir for 1 h further at 90° C. Exact amounts of ingredients in percent by weight of the ink are shown in the table below.

INK EXAMPLES F THROUGH J

The amide gellant synthesized in Example VIII and propoxylated neopentyl glycol diacrylate.(SR9003, obtained from Sartomer Co. Inc., Exton, Pa.) were combined and stirred at 90° C. for 1 h. The resulting mixture was filtered to 0.22 μm at 90° C., let cool to room temperature overnight, remelted, and filtered to 0.22 μm at 90° C. To the resulting solution was then added 2-dimethylamino-2-(4-methylbenzyl)-1-(4-morpholin-4-ylphenyl)-butanone (IRGACURE® 379, obtained from Ciba Specialty Chemicals, Tarrytown, N.Y.), isopropyl-9H-thioxanthen-9-one (DAROCUR® ITX, obtained from Ciba Specialty Chemicals, Tarrytown, N.Y.), bis(2,4,6-trimethylbenzoyl)-phenyl-phosphine oxide (IRGACURE® 819, obtained from Ciba Specialty Chemicals, Tarrytown, N.Y.), 2-hydroxy-1-(4-(4-(2-hydroxy-2-methyl-propionyl)-benzyl)-phenyl)-2-methylpropan-1-one (IRGACURE® 127, obtained from Ciba Specialty Chemicals, Tarrytown, N.Y.), and IRGASTAB® UV10 (obtained from Ciba Specialty Chemicals, Tarrytown, N.Y.), and the entire solution was stirred for 1 h at 90° C. The ink base thus prepared was then filtered to 0.22 μm and the hot solution (90° C.) was added dropwise to a stirring solution of the desired pigment dispersion (SUN BLUE pigment dispersion, 25 wt %, obtained from Sun Chemical, Parsippany, N.J., SUN YELLOW pigment dispersion, 16 wt %, obtained from Sun Chemical, Parsippany, N.J., SUN MAGENTA pigment dispersion, 21 wt %, obtained from Sun Chemical, Parsippany, N.J., or SUN BLACK pigment dispersion, 26.5 wt %, obtained from Sun Chemical, Parsippany, N.J.), also at 90° C. The resulting inks were then filtered to 6 μm. Exact amounts of ingredients in percent by weight of the ink are shown in the table below.

| Component | Wt % Ink A | Wt % Ink B | Wt % Ink C | Wt % Ink D | Wt % Ink E | Wt % Ink F | Wt % Ink G | Wt % Ink H | Wt % Ink J |
|---|---|---|---|---|---|---|---|---|---|
| SR9003 | 70.8 | 70.8 | 70.8 | 70.8 | 70.8 | 70.8 | 63.8 | 68.5 | 71.5 |
| gellant, Example I | 7.5 | 0 | 0 | 0 | 0 | 0 | 0 | 0 | 0 |
| gellant, Example VIII | 0 | 0 | 0 | 0 | 0 | 7.5 | 7.5 | 7.5 | 7.5 |
| gellant, Example IV | 0 | 7.5 | 0 | 0 | 0 | 0 | 0 | 0 | 0 |
| gellant, Example V | 0 | 0 | 7.5 | 0 | 0 | 0 | 0 | 0 | 0 |
| gellant, Example VI | 0 | 0 | 0 | 7.5 | 0 | 0 | 0 | 0 | 0 |
| gellant, Example VII | 0 | 0 | 0 | 0 | 7.5 | 0 | 0 | 0 | 0 |
| IRGACURE ® 379 | 3.0 | 3.0 | 3.0 | 3.0 | 3.0 | 3.0 | 3.0 | 3.0 | 3.0 |
| DAROCUR ® ITX | 2.0 | 2.0 | 2.0 | 2.0 | 2.0 | 2.0 | 2.0 | 2.0 | 2.0 |
| IRGACURE ® 819 | 1.0 | 1.0 | 1.0 | 1.0 | 1.0 | 1.0 | 1.0 | 1.0 | 1.0 |
| IRGACURE 127 | 3.5 | 3.5 | 3.5 | 3.5 | 3.5 | 3.5 | 3.5 | 3.5 | 3.5 |
| IRGASTAB ® UV10 | 0.2 | 0.2 | 0.2 | 0.2 | 0.2 | 0.2 | 0.2 | 0.2 | 0.2 |
| SUN BLUE | 12.0 | 12.0 | 12.0 | 12.0 | 12.0 | 12.0 | 0 | 0 | 0 |
| SUN YELLOW | 0 | 0 | 0 | 0 | 0 | 0 | 19.0 | 0 | 0 |
| SUN MAGENTA | 0 | 0 | 0 | 0 | 0 | 0 | 0 | 14.3 | 0 |
| SUN BLACK | 0 | 0 | 0 | 0 | 0 | 0 | 0 | 0 | 11.3 |

Rheological characteristics of Inks A through J were obtained by testing with a Rheometrics Fluid Spectrometer RFS3. A temperature sweep from 90° C. to 30° C. at 1 Hz sweep rate was conducted with measurements every five degrees.

Complex viscosity ($\eta$, centipoise) of the inks at various temperatures is given in the tables below:

| ° C. | $\eta$ Ink A | $\eta$ Ink B | $\eta$ Ink C | $\eta$ Ink D | $\eta$ Ink E |
|---|---|---|---|---|---|
| 90 | 5.8717 | 4.5537 | 5.5677 | 6.8639 | 5.3605 |
| 85 | 6.8514 | 4.8638 | 6.2424 | 6.6716 | 6.7935 |
| 80 | 7.9712 | 5.7897 | 7.01E+00 | 7.3701 | 7.8864 |
| 75 | 98.52 | 6.5498 | 8.24E+00 | 8.5278 | 8.95E+00 |
| 70 | 6156.5 | 9.6933 | 20.458 | 32.674 | 2.10E+01 |
| 65 | 1.49E+04 | 1.01E+03 | 1810.9 | 1856.3 | 1.67E+03 |
| 60 | 8.86E+04 | 3.28E+04 | 47721 | 56750 | 49436 |
| 55 | 2.51E+05 | 1.50E+05 | 2.11E+05 | 2.19E+05 | 2.23E+05 |
| 50 | 5.31E+05 | 3.60E+05 | 5.06E+05 | 2.07E+05 | 5.40E+05 |
| 45 | 9.51E+05 | 6.32E+05 | 9.11E+05 | 2.54E+05 | 1.02E+06 |
| 40 | 1.49E+06 | 9.55E+05 | 1.44E+06 | 4.13E+05 | 1.64E+06 |
| 35 | 2.11E+06 | 9.48E+05 | 2.05E+06 | 6.21E+05 | 2.42E+06 |
| 30 | 2.76E+06 | 1.19E+06 | 2.77E+06 | 8.52E+05 | 3.35E+06 |

| ° C. | $\eta$ Ink F | $\eta$ Ink G | $\eta$ Ink H | $\eta$ Ink J |
|---|---|---|---|---|
| 90 | 6.4372 | 6.8538 | 6.947 | 4.5915 |
| 85 | 7.093 | 7.863 | 7.7231 | 5.073 |
| 80 | 7.9503 | 8.6261 | 8.8969 | 5.5286 |
| 75 | 9.0937 | 10.045 | 10.266 | 6.5031 |
| 70 | 11.457 | 11.542 | 11.961 | 8.0366 |
| 65 | 1396.2 | 741.17 | 533.16 | 682.01 |
| 60 | 6.86E+04 | 8.10E+04 | 4.61E+04 | 1.25E+04 |
| 55 | 2.53E+05 | 2.43E+05 | 1.76E+05 | 8.02E+04 |
| 50 | 5.21E+05 | 5.22E+05 | 3.86E+05 | 1.76E+05 |
| 45 | 9.09E+05 | 9.31E+05 | 7.07E+05 | 2.95E+05 |
| 40 | 1.44E+06 | 1.49E+06 | 1.16E+06 | 4.41E+05 |
| 35 | 2.13E+06 | 2.20E+06 | 1.73E+06 | 6.17E+05 |
| 30 | 2.93E+06 | 3.01E+06 | 2.43E+06 | 8.07E+05 |

Inks F, G, H and J were jetted using a PHASER® 860 printer modified to change the intermediate transfer drum temperature, paper preheating temperature, and ink heating temperature and printed at temperatures ranging from 75 to 85° C. directly onto paper attached to an intermediate transfer member at 30° C. The inks were successfully jetted onto XEROX® DIGITAL COLOR GLOSS glossy coated paper and HAMMERMILL® (International Paper) and XEROX® 4024 uncoated papers. The amount of showthrough (degree to which the printed image was visible on the surface of the paper opposite to that on which the image was printed) increased as follows: XEROX DIGITAL COLOR GLOSS®<HAMMERMILL® <XEROX®4024. In each case, when the prints were exposed to light from a UV Fusion LC-6B Benchtop Conveyor equipped with UV Fusion F300S Ultraviolet Lamp System employing a "D" bulb for a minimum of 2 to 3 seconds, the prints could neither be scratched nor smudged.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A compound of the formula

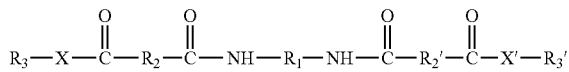

wherein $R_1$ is (i) a linear or branched alkylene group, which can be saturated or unsaturated, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is an oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group.

2. A compound according to claim 1 wherein $R_2$ and $R_2'$ are the same as each other.

3. A compound according to claim 1 wherein $R_3$ and $R_3'$ are the same as each other.

4. A compound according to claim 1 wherein $R_2$ and $R_2'$ are the same as each other and wherein $R_3$ and $R_3'$ are the same as each other.

5. A compound according to claim 1 wherein $R_1$ is an alkylene group.

6. A compound according to claim 5 wherein the alkylene group is a saturated alkylene group.

7. A compound according to claim 5 wherein the alkylene group is an unsubstituted alkylene group.

8. A compound according to claim 1 wherein $R_1$ is a —$CH_2CH_2$— group.

9. A compound according to claim 1 wherein $R_2$ and $R_2'$ are each alkylene groups.

10. A compound according to claim 9 wherein the alkylene groups are saturated alkylene groups.

11. A compound according to claim 9 wherein the alkylene groups are unsubstituted alkylene groups.

12. A compound of the formula

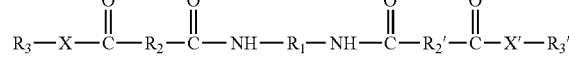

wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ are each groups of the formula —$C_{34}H_{56+a}$— and are branched alkylene groups which may include unsaturations and cyclic groups, wherein a is an integer of 0, 1, 2, 3, 4, 5, 6, 7, 8, 9, 10, 11, or 12, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is an oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted, or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group.

13. A compound according to claim 12 wherein $R_2$ and $R_2'$ are each groups of the formula

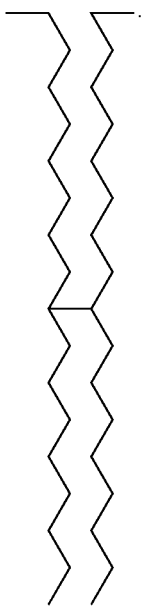

14. A compound of the formula

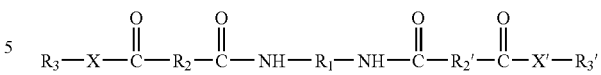

wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is an oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, wherein at least one of $R_3$ and $R_3'$ are groups of the formula

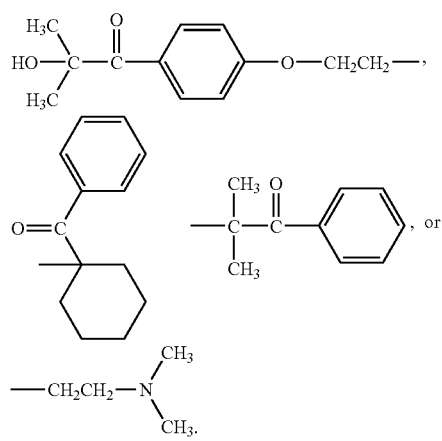

15. A compound according to claim 1 wherein X and X' are each oxygen atoms.

16. A compound of the formula

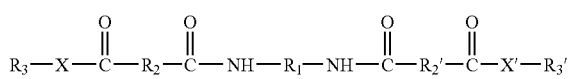

wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene group, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is a group of the formula $-NR_4-$, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group.

17. A compound according to claim 16 wherein $R_4$ is a hydrogen atom or an alkyl group.

18. A compound according to claim 1 of the formula
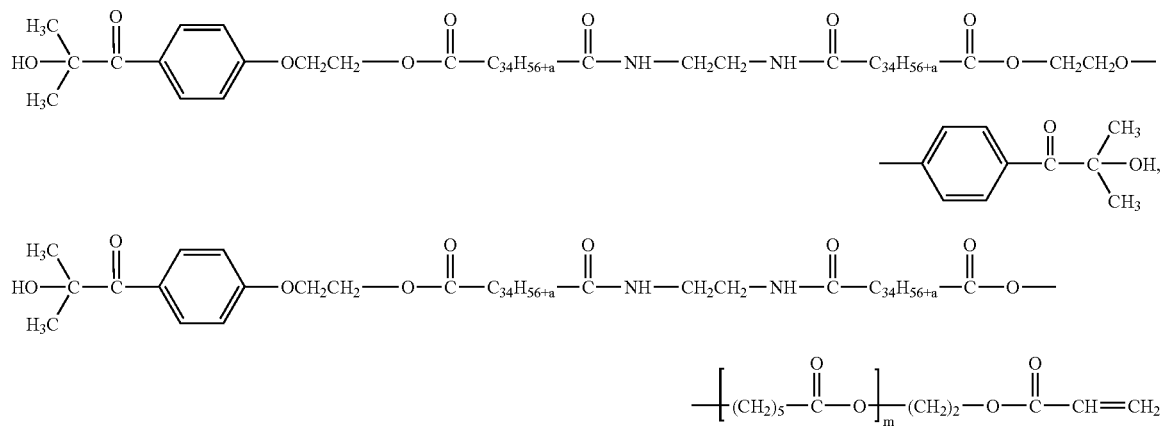
wherein m is an integer,
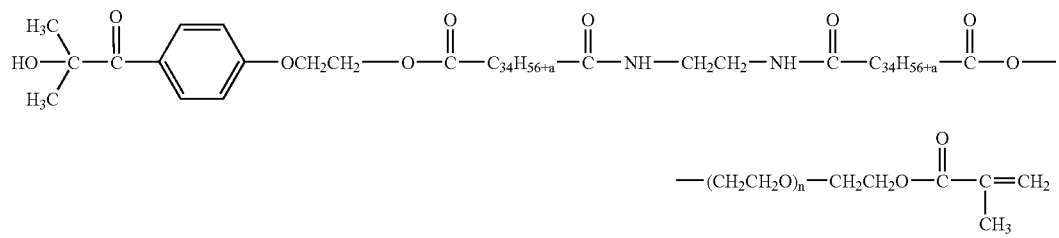
wherein n is an integer,
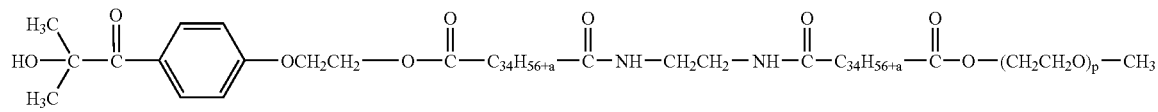
wherein p is an integer,
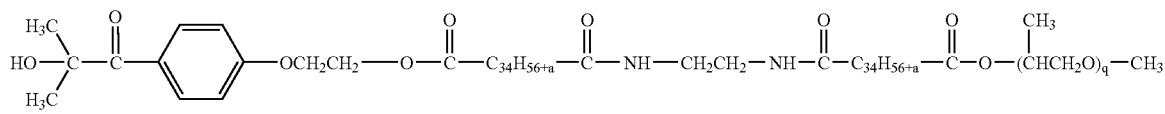
wherein q is an integer,
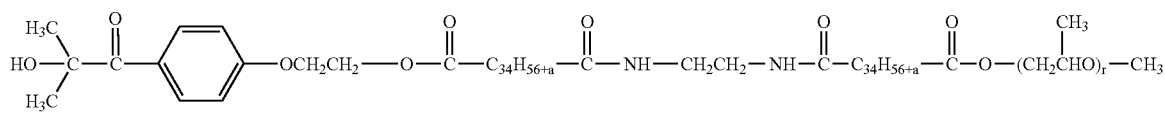
wherein r is an integer,

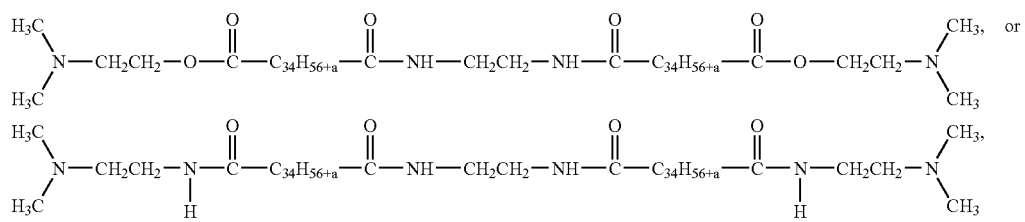
wherein —C₃₄H₅₆₊ₐ— represents a branched alkylene group which may be unsaturated and/or cyclic groups, wherein a is an integer of 0, 1, 2, 3, 4, 5, 6, 7, 8, 9, 10, 11, or 12.
19. A compound according to claim 1 of the formula
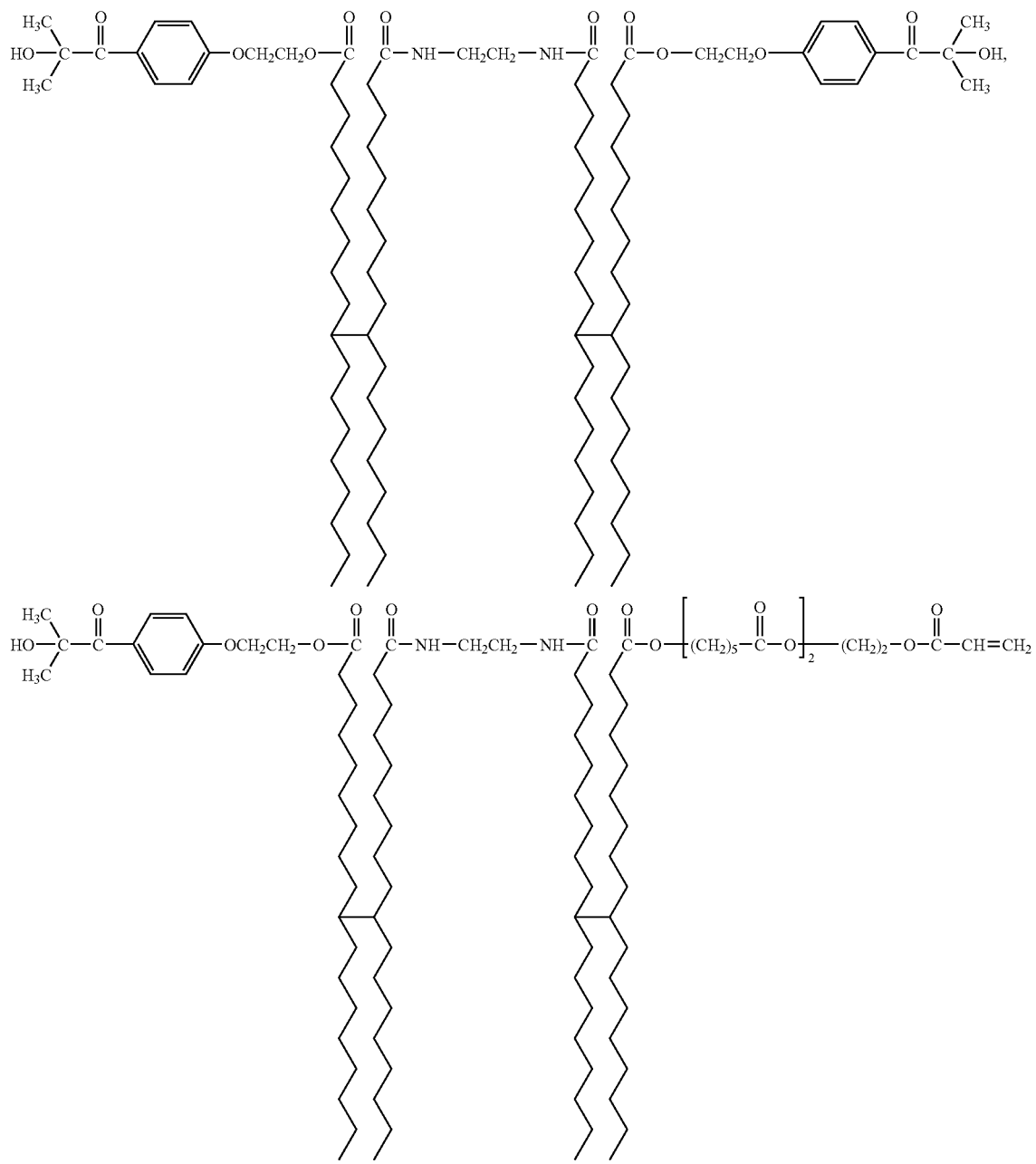
wherein m is an integer,

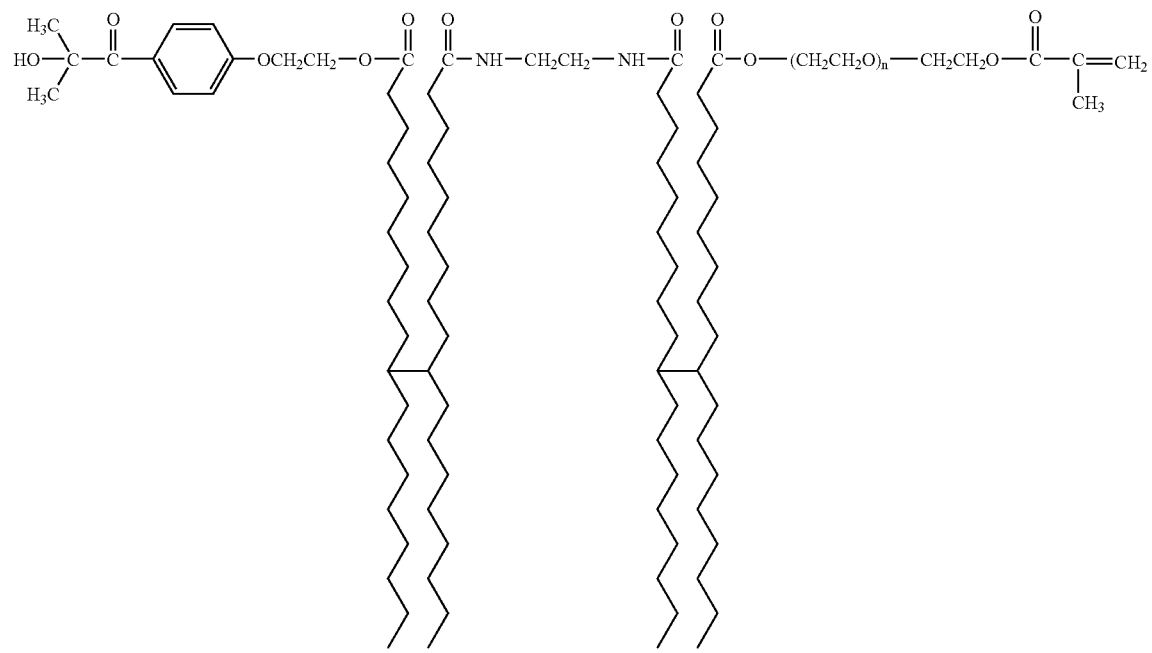
wherein n is an integer,
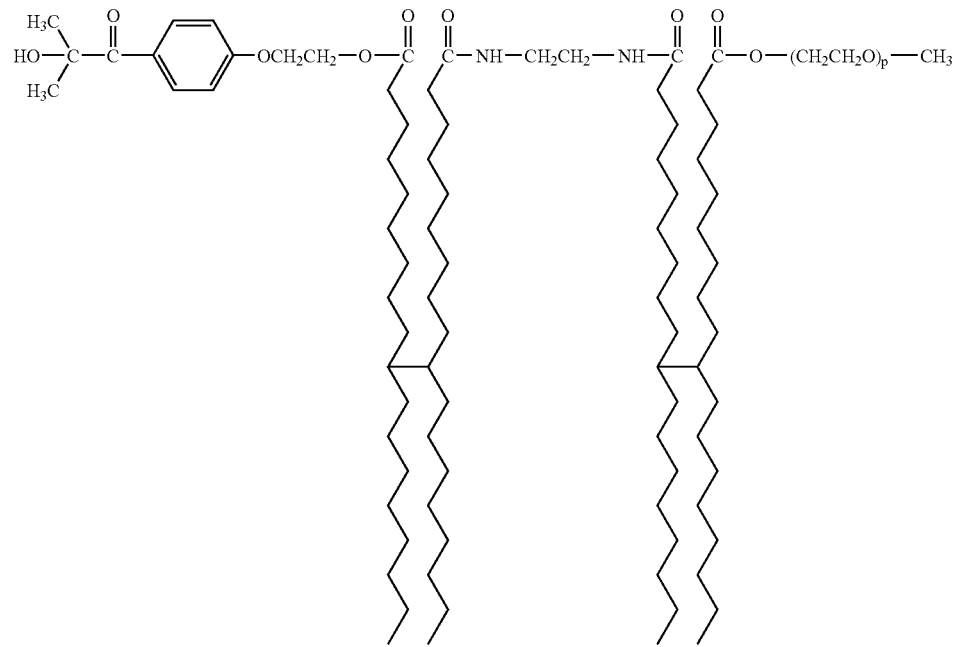
wherein p is an integer,

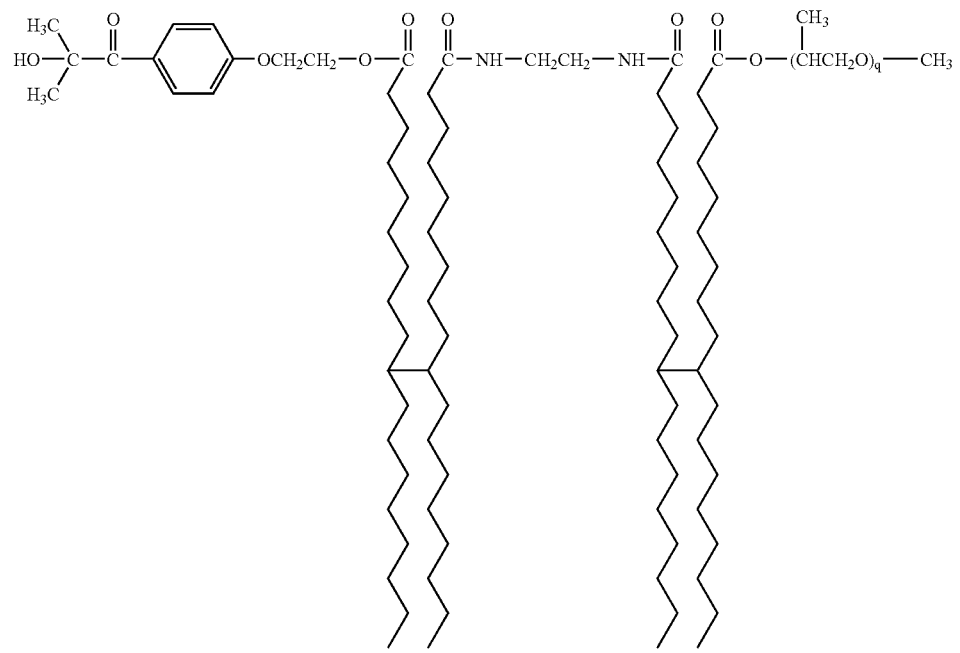
wherein q is an integer,
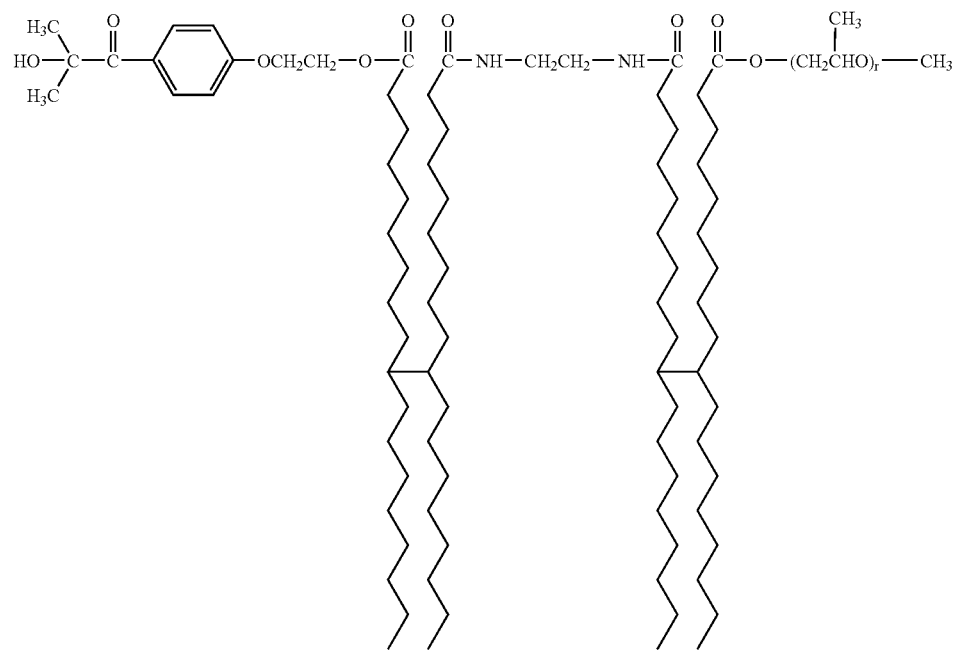
wherein r is an integer,

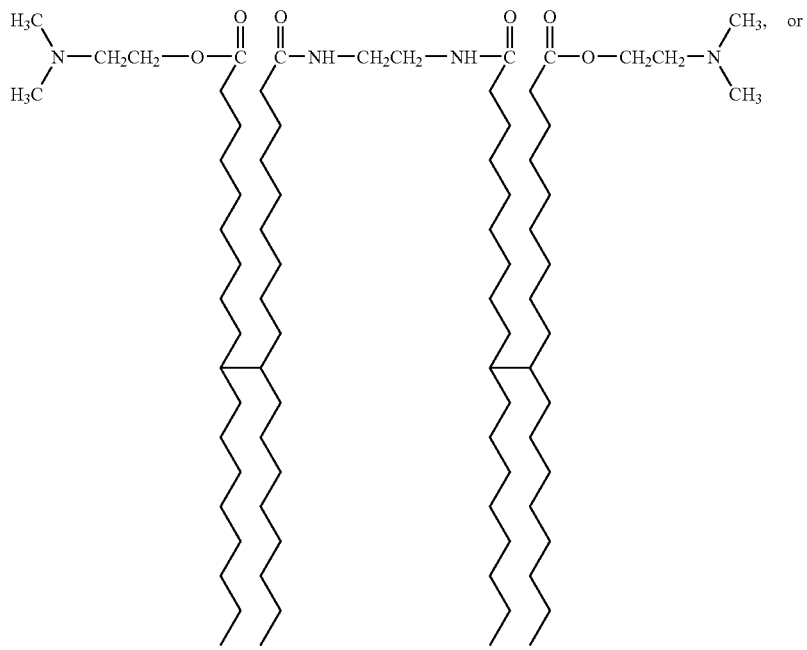
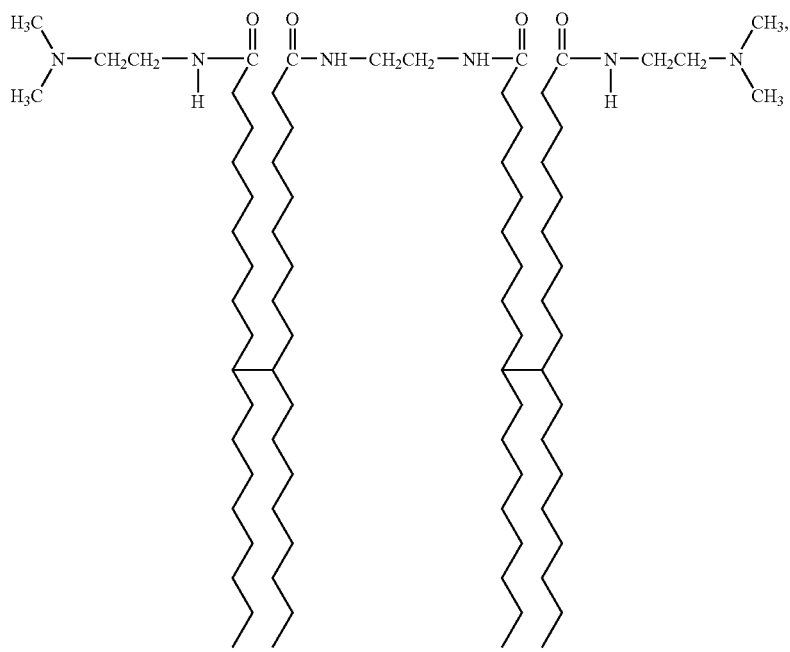
20. A compound according to claim 14 wherein at least one of $R_3$ and $R_3'$ is
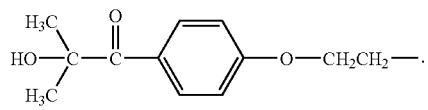
21. A compound of the formula
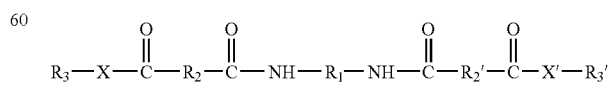
wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is on oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, wherein $R_2$ and $R_2'$ are different from each other.

22. A compound of the formula $$R_3-X-\overset{O}{\underset{\|}{C}}-R_2-\overset{O}{\underset{\|}{C}}-NH-R_1-NH-\overset{O}{\underset{\|}{C}}-R_2'-\overset{O}{\underset{\|}{C}}-X'-R_3'$$

wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is on oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, wherein $R_2$ and $R_2'$ are different from each other.

23. A compound of the formula

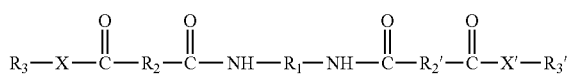

wherein $R_1$ is (i) an alkylene group, which can be linear or branched, saturated or unsaturated, cyclic or acyclic, and substituted or unsubstituted alkylene groups, and wherein hetero atoms either may or may not be present in the alkylene group, (ii) an arylene group, which can be substituted or unsubstituted arylene groups, and wherein hetero atoms either may or may not be present in the arylene group, (iii) an arylalkylene group, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) an alkylarylene group, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_2$ and $R_2'$ each, independently of the other, are (i) alkylene groups, which can be linear or branched, saturated or unsaturated, cyclic or acyclic, and substituted or unsubstituted alkylene groups, and wherein hetero atoms either may or may not be present in the alkylene group, (ii) arylene groups, which can be substituted or unsubstituted arylene groups, and wherein hetero atoms either may or may not be present in the arylene group, (iii) arylalkylene groups, which can be substituted or unsubstituted arylalkylene groups, wherein the alkyl portion of the arylalkylene group can be linear or branched, saturated or unsaturated, and cyclic or acyclic, and wherein hetero atoms either may or may not be present in either the aryl or the alkyl portion of the arylalkylene group, or (iv) alkylarylene groups, which can be substituted or unsubstituted alkylarylene groups, wherein the alkyl portion of the alkylarylene group can be linear or branched, saturated or unsaturated, and cyclic or acyclic, and wherein hetero atoms either may or may not be present in either the aryl or the alkyl portion of the alkylarylene group, $R_3$ and $R_3'$ each, independently of the other, are either (a) photoinitiating groups, or (b) groups which are (i) alkyl groups, which can be linear or branched, saturated or unsaturated, cyclic or acyclic, and substituted or unsubstituted alkyl groups, and wherein hetero atoms either may or may not be present in the alkyl group, (ii) aryl groups, which can be substituted or unsubstituted aryl groups, wherein hetero atoms either may or may not be present in the aryl group, (iii) arylalkyl groups, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (iv) alkylaryl groups, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, provided that at least one of $R_3$ and $R_3'$ is a photoinitiating group, and X and X' each, independently of the other, is on oxygen atom or a group of the formula —$NR_4$—, wherein $R_4$ is (i) a hydrogen atom, (ii) an alkyl group, which can be linear or branched, saturated or unsaturated, cyclic or acyclic, and substituted or unsubstituted alkyl groups, and wherein hetero atoms either may or may not be present in the alkyl group, (iii) an aryl group, which can be substituted or unsubstituted aryl groups, and wherein hetero atoms either may or may not be present in the aryl group, (iv) an arylalkyl group, which can be substituted or unsubstituted arylalkyl groups, wherein the alkyl portion of the arylalkyl group can be linear or branched, saturated or unsaturated, and cyclic or acyclic, and wherein hetero atoms either may or may not be present in either the aryl or the alkyl portion of the arylalkyl group, or (v) an alkylaryl group, which can be substituted or unsubstituted alkylaryl groups, wherein the alkyl portion of the alkylaryl group can be linear or branched, saturated or unsaturated, and cyclic or acyclic, and wherein hetero atoms either may or may not be present in either the aryl or the alkyl portion of the alkylaryl group, wherein $R_2$ and $R_2'$ are different from each other.

* * * * *